US006743792B2

(12) United States Patent
Freyne et al.

(10) Patent No.: US 6,743,792 B2
(45) Date of Patent: Jun. 1, 2004

(54) 6-AZAURACIL DERIVATIVES AS IL-5 INHIBITORS

(75) Inventors: Eddy Jean Edgard Freyne, Rumst (BE); Gustaaf Maria Boeckx, Oud-Turnhout (BE); Jean Pierre Frans Van Wauwe, Beerse (BE); Gaston Stanislas Marcella Diels, Ravels (BE)

(73) Assignee: Janssen Pharmaceutica N.V. (BE)

( * ) Notice: Subject to any disclaimer, the term of this patent is extended or adjusted under 35 U.S.C. 154(b) by 0 days.

(21) Appl. No.: 09/855,068

(22) Filed: May 14, 2001

(65) Prior Publication Data

US 2002/0042416 A1 Apr. 11, 2002

Related U.S. Application Data

(63) Continuation of application No. 09/462,323, filed on Jan. 5, 2000, now abandoned, which is a continuation of application No. PCT/EP98/04192, filed on Jul. 2, 1998.

(30) Foreign Application Priority Data

Jul. 10, 1997 (EP) .......................................... 97.202.117

(51) Int. Cl.$^7$ .................... C07D 253/075; A61K 31/53; A61P 11/06; A61P 37/08

(52) U.S. Cl. ................. 514/242; 514/227.8; 514/235.8; 544/182; 544/60; 544/112

(58) Field of Search ........................... 544/182, 60, 112, 544/242; 514/242, 227.8, 235.8

(56) References Cited

U.S. PATENT DOCUMENTS

| | | | |
|---|---|---|---|
| 3,883,527 A | 5/1975 | Brennan | |
| 4,631,278 A | 12/1986 | Boeckx et al. | |
| 4,767,760 A | 8/1988 | Boeckx et al. | |
| 4,931,444 A | 6/1990 | Van Wauwe et al. | |
| 5,256,631 A | * 10/1993 | Lindner et al. | 544/182 |

FOREIGN PATENT DOCUMENTS

| | | |
|---|---|---|
| EP | 0 232 932 A1 * | 8/1987 |
| EP | 476 439 | 3/1992 |
| EP | 737 672 | 10/1996 |
| WO | WO 94/14742 | 7/1994 |
| WO | WO 94/20446 | 9/1994 |
| WO | WO 96/31485 | 10/1996 |

OTHER PUBLICATIONS

Carroll et al., J. Med. Chem. 1983, 26, 96–100.
Carr et al., Immunology, 1994, 91, 3652–3656.
Baggiolini et al., Immunology Today, 1994, 15(3), 127–133.
U.S.S.N. 09/891,888 (containing the claims as pending).
PCT International Search Report dated Oct. 28, 1998 for PCT Appln. No. PCT/EP98/04192 which relates to U.S. Patent Appln. No. 09/855,068.

* cited by examiner

*Primary Examiner*—Richard L. Raymond
*Assistant Examiner*—Venkataraman Balasubramanian
(74) *Attorney, Agent, or Firm*—Alana G. Kriegsman; Ellen Ciambrone Coletti

(57) ABSTRACT

The present invention is concerned with the use of compounds of formula (I)

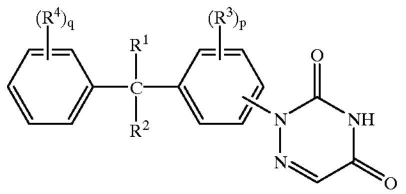

the N-oxides, the pharmaceutically acceptable addition salts and the stereochemically isomeric forms thereof, wherein p represents 0, 1, 2 or 3; q represents 0, 1, 2, 3 or 4; $R^1$ represents hydrogen, $C_{1-6}$alkyl, mono- or di($C_{1-6}$alkyl) amino$C_{1-6}$alkyloxy, mercapto, $C_{1-6}$alkylthio, $C_{3-7}$cycloalkyl, aryl or $C_{1-6}$alkyl substituted with mono- or di($C_{1-6}$alkyl)-amino, $C_{1-6}$alkyloxy, aryl or Het; $R^2$ represents cyano or a radical of formula —C(=X)—Y—$R^5$; wherein X represents O or S; Y represents O, S, $NR^6$ or a direct bond; $R^5$ represents hydrogen; $C_{3-7}$cycloalkyl; aryl or optionally substituted $C_{1-6}$alkyl; and where Y is a direct bond, $R^5$ may also be halo or Het; $R^3$ and $R^4$ each independently represents halo, halo$C_{1-6}$alkyl, $C_{1-6}$alkyl, hydroxy, $C_{1-6}$alkyloxy, $C_{1-6}$alkylcarbonyloxy, mercapto, $C_{1-6}$alkylthio, $C_{1-6}$alkylsulfonyl, $C_{1-6}$alkylsulfinyl, halo$C_{1-6}$alkylsulfonyl, aryl, cyano, nitro, amino, mono- and di($C_{1-6}$alkyl)amino or ($C_{1-6}$alkylcarbonyl)amino; aryl represents phenyl or substituted phenyl; and Het represents an optionally substituted heterocycle; in the manufacture of a medicament useful for treating eosinophil-dependent inflammatory diseases. The invention also relates to novel compounds, their preparation and compositions comprising them.

18 Claims, No Drawings

6-AZAURACIL DERIVATIVES AS IL-5 INHIBITORS

CROSS REFERENCE TO RELATED APPLICATIONS

This application is a continuation of application Serial No. 09/462,323 filed on Jan. 5, 2000, now abandoned, which is the National Stage application under 35 U.S.C. 371 of PCT/EP98/04192 filed Jul. 2, 1998, which claims priority from EP 97.202.117.4, filed Jul. 10, 1997.

The present invention concerns the use of IL-5 inhibiting 6-azauracil derivatives in the manufacture of a medicament useful for treating eosinophil-dependent inflammatory diseases. It further relates to certain novel 6-azauracil derivatives, to processes for their preparation and compositions comprising them.

Eosinophil influx, leading to subsequent tissue damage, is an important pathogenic event in bronchial asthma and allergic diseases. The cytokine interleukin-5 (IL-5), produced mainly by T lymphocytes as a glycoprotein, induces the differentiation of eosinophils in bone marrow and, primes eosinophils for activation in peripheral blood and sustains their survival in tissues. As such, IL-5 plays a critical role in the process of eosinophilic inflammation. Hence, the possibility that inhibitors of IL-5 production would reduce the production, activation and/or survival of eosinophils provides a therapeutic approach to the treatment of bronchial asthma and allergic diseases such as, atopic dermatitis, allergic rhinitis, allergic conjunctivitis, and also other eosinophil-dependent inflammatory diseases.

Steroids, which strongly inhibit IL-5 production in vitro, have long been used as the only drugs with remarkable efficacy for bronchial asthma and atopic dermatitis, but they cause various serious adverse reactions such as diabetes, hypertension and cataracts. Therefore, it would be desirable to find non-steroidal compounds having the ability to inhibit IL-5 production in human T-cells and which have little or no adverse reactions.

U.S. Pat. No. 4,631,278 discloses α-aryl-4-(4,5-dihydro-3,5-dioxo-1,2,4-triazin-2(3H)-yl)-benzeneacetonitriles and U.S. Pat. No. 4,767,760 discloses 2-(substituted phenyl)-1,2,4-triazine-3,5(2H,4H)-diones, all having anti-protozoal activity, in particular, anti-coccidial activity. Unexpectedly, the 6-azauracil derivatives of the present invention, including said art-known 1,2,4-triazinedione derivatives, prove to be potent inhibitors of the production of IL-5.

The present invention is concerned with the use of compounds of formula (I)

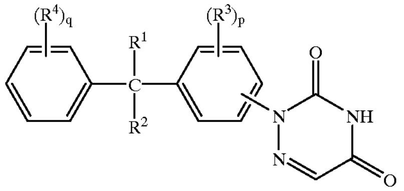

the N-oxides, the pharmaceutically acceptable addition salts and the stereochemically isomeric forms thereof, wherein:

p represents an integer being 0, 1, 2, 3 or 4;

q represents an integer being 0, 1, 2, 3, 4 or 5;

$R^1$ represents hydrogen, $C_{1-6}$alkyl, mono- or di($C_{1-6}$alkyl)amino$C_{1-6}$alkyloxy, mercapto, $C_{1-6}$alkylthio, $C_{3-7}$cycloalkyl, aryl or $C_{1-6}$alkyl substituted with mono- or di($C_{1-6}$alkyl)amino, $C_{1-6}$alkyloxy, aryl or Het;

$R^2$ represents cyano or a radical of formula —C(=X)—Y—$R^5$; wherein

X represents O or S;

Y represents O, S, $NR^6$ or a direct bond;

$R^5$ represents hydrogen; $C_{1-6}$alkyl; $C_{3-7}$cycloalkyl; aryl or $C_{1-6}$alkyl substituted with aryl, hydroxy or Het; and where Y is a direct bond, $R^5$ may also be halo or Het;

$R^6$ represents hydrogen, $C_{1-6}$alkyl, $C_{1-6}$alkyloxy or aryl$C_{1-6}$alkyl;

each $R^3$ independently represents halo, halo$C_{1-6}$alkyl, $C_{1-6}$alkyl, hydroxy, $C_{1-6}$alkyloxy, $C_{1-6}$alkylcarbonyloxy, mercapto, $C_{1-6}$alkylthio, $C_{1-6}$alkylsulfonyl, $C_{1-6}$alkylsulfinyl, halo$C_{1-6}$alkylsulfonyl, aryl, cyano, nitro, amino, mono- and di($C_{1-6}$alkyl)amino or ($C_{1-6}$alkylcarbonyl)amino;

each $R^4$ independently represents halo, halo$C_{1-6}$alkyl, $C_{1-6}$alkyl, hydroxy, $C_{1-6}$alkyloxy, $C_{1-6}$alkylcarbonyloxy, mercapto, $C_{1-6}$alkylthio, $C_{1-6}$alkylsulfonyl, $C_{1-6}$alkylsulfinyl, halo$C_{1-6}$alkylsulfonyl, aryl, cyano, nitro, amino, mono- and di($C_{1-6}$alkyl)amino or ($C_{1-6}$alkylcarbonyl)amino;

aryl represents phenyl or phenyl substituted with one, two or three substituents selected from the group comprising halo, $C_{1-6}$alkyl, $C_{1-6}$alkyloxy, halo$C_{1-6}$alkyl, hydroxy, mercapto, $C_{1-6}$alkylthio, $C_{1-6}$alkylsulfonyl, $C_{1-6}$alkylsulfonyloxy, $C_{1-6}$alkylsulfinyl, halo$C_{1-6}$alkylsulfonyl, nitro, cyano, amino, mono- and di($C_{1-6}$alkyl)amino and $C_{1-6}$alkylcarbonylamino; and Het represents a heterocycle selected from pyrrolyl, pyrrolinyl, pyrrolidinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, piperidinyl, piperazinyl, morpholinyl, thiomorpholinyl, dioxanyl, dithianyl, trithianyl, triazinyl, benzothienyl, isobenzothienyl, benzofuranyl, isobenzofuranyl, benzthiazolyl, benzoxazolyl, indolyl, isoindolyl, indolinyl, purinyl, benzimidazolyl, quinolyl, isoquinolyl, cinnolinyl, phtalazinyl, quinazolinyl, quinoxalinyl and thiazolopyridinyl; said heterocycles each independently may be substituted with one, two or three substituents selected from hydroxy, mercapto, $C_{1-4}$alkyl, $C_{1-4}$alkyloxy, cyano, amino, nitro, mono- or di($C_{1-4}$alkyl)amino, mono- or di($C_{1-4}$alkyl)aminocarbonyl, mono- or di(aryl)amino, halo, halo$C_{1-4}$alkyl, $C_{1-4}$alkyloxycarbonyl, aryl, furanyl, thienyl, pyridinyl, piperidinyl, $C_{1-4}$alkylcarbonylpiperidinyl and $C_{1-4}$alkyl substituted with hydroxy, $C_{1-4}$alkyloxy, aryl, piperidinyl, amino, mono- or di($C_{1-4}$alkyl)amino or $C_{3-7}$cycloalkyl;

in the manufacture of a medicament useful for treating eosinophil-dependent inflammatory diseases.

The compounds of formula (I) are deemed novel, provided that the α-aryl-4-(4,5-dihydro-3,5-dioxo-1,2,4-triazin-2(3H)-yl)benzeneacetonitriles published in U.S. Pat. No. 4,631,278 and the 2-(substituted phenyl)-1,2,4-triazine-3,5(2H,4H)-diones published in U.S. Pat. No. 4,767,760 are excluded therefrom.

Thus, the invention also concerns novel compounds of formula (I')

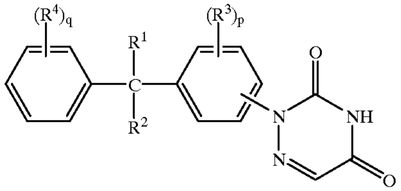

the N-oxides, the pharmaceutically acceptable addition salts and the stereochemically isomeric forms thereof, wherein p, q, $R^1$, $R^2$, $R^3$ and $R^4$ are as defined in the compounds of formula (I), provided that the following conditions apply to the variables $R^{3a}$, $R^{3b}$, $R^{3c}$, $R^{4a}$, $R^{4b}$, $R^{4c}$, $R^1$ and $R^2$ in the compounds with general structure:

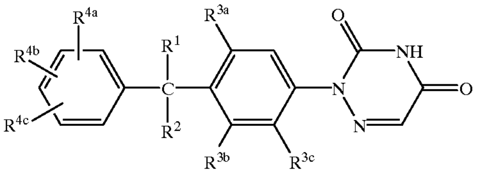

a) if $R^{3a}$, $R^{3b}$ are chloro; $R^{4a}$ is 4-chloro; and $R^1$, $R^{3c}$, $R^{4b}$ and $R^{4c}$ are hydrogen; then $R^2$ is other than aminocarbonyl, carboxyl, chlorocarbonyl, 1-piperidinylcarbonyl, methoxycarbonyl, methylaminocarbonyl, 1-pyrrolidinylcarbonyl, 4-methyl-1-piperazinylcarbonyl, methylcarbonyl, $NH_2—C(=S)—$, phenylcarbonyl; and b) if $R^{3a}$ is chloro; $R^{4a}$ is 4-chloro; and $R^1$, $R^{3b}$, $R^{3c}$, $R^{4b}$ and $R^{4c}$ are hydrogen; then $R^2$ is other than aminocarbonyl, carboxyl, $NH_2—C(=S)—$, chlorocarbonyl, methylaminocarbonyl, (4-methylcarbonyl-1-piperazinyl)carbonyl, (4-phenylmethyl-1-piperazinyl)carbonyl or methyloxycarbonyl; and c) if the combination of $R^1$, $R^{3a}$, $R^{3b}$, $R^{3c}$, $R^{4a}$, $R^{4b}$ and $R^{4c}$ is one of the following

| $R^1$ | $R^{3a}$ | $R^{3b}$ | $R^{3c}$ | $R^{4a}$ | $R^{4b}$ | $R^{4c}$ |
|---|---|---|---|---|---|---|
| 4-chlorophenyl | Cl | H | H | H | 4-Cl | H |
| 1-propyl | Cl | H | H | H | 4-Cl | H |
| 1-butyl | Cl | H | H | H | 4-Cl | H |
| $CH_3$ | Cl | H | H | H | 4-Cl | H |
| $CH_3$ | H | H | H | H | 4-H | H |
| $CH_3$ | H | Cl | H | H | 4-F | H |
| $CH_3$ | $CF_3$ | H | H | H | 4-Cl | H |
| $CH_3$ | Cl | H | H | 3-$CF_3$ | 4-Cl | H |
| $CH_3$ | Cl | Cl | H | H | 4-Cl | H |
| $CH_3$ | Cl | $CH_3$ | H | H | 4-Cl | H |
| $CH_3$ | F | H | H | H | 4-F | H |
| H | Cl | $CH_3$ | H | H | 4-Cl | H |
| H | Cl | H | H | H | 4-F | H |
| H | Cl | H | H | H | 4-$CH_3$ | H |
| H | Cl | Cl | H | H | 4-F | H |
| H | Cl | $CH_3$ | H | H | 4-F | H |
| H | $CH_3$ | $CH_3$ | H | H | 4-F | H |
| H | $CH_3$ | $CH_3$ | H | H | 4-Cl | H |
| H | Cl | Cl | H | H | 4-Cl | H |
| H | Cl | H | H | H | 4-Cl | H |

-continued

| $R^1$ | $R^{3a}$ | $R^{3b}$ | $R^{3c}$ | $R^{4a}$ | $R^{4b}$ | $R^{4c}$ |
|---|---|---|---|---|---|---|
| H | Cl | H | H | 2-Cl | 4-Cl | H |
| H | Cl | H | H | 2-Cl | 4-Cl | 6-Cl |
| H | Cl | H | H | H | 4-Br | H |
| H | Cl | Cl | H | H | 4-Br | H |
| H | Cl | Cl | H | H | 4-$CH_3C(=O)O$ | H |
| H | Cl | Cl | H | H | 4-OH | H |
| H | OH | H | H | H | 4-Cl | H |
| H | Cl | H | H | H | 4-$CH_3S$ | H |
| H | Cl | Cl | H | H | 4-$CH_3S$ | H |
| H | $CH_3$ | $CH_3$ | H | H | 4-$CH_3S$ | H |
| H | Cl | H | H | 3-$CH_3$ | 4-$CH_3S$ | H |
| H | Cl | Cl | H | 3-$CH_3$ | 4-$CH_3S$ | H |
| H | Cl | H | H | H | 4-$CH_3SO$ | H |
| H | Cl | Cl | H | H | 4-$CH_3SO$ | H |
| H | Cl | H | H | H | 4-$CH_3S(O)_2$ | H |
| H | Cl | Cl | H | H | 4-$CH_3S(O)_2$ | H |
| H | Cl | H | H | H | 4-SH | H |
| H | Cl | Cl | H | H | 4-SH | H |
| $CH_3$ | Cl | H | $CH_3$ | 4-Cl | H | H |
| H | H | H | $OCH_3$ | 4-Cl | H | H |

then $R^2$ is other than cyano.

As used in the foregoing definitions and hereinafter, halo is generic to fluoro, chloro, bromo and iodo; $C_{3-7}$cycloalkyl is generic to cyclopropyl, cyclobutyl, cyclopentyl, cyclohexyl and cycloheptyl; $C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like; $C_{1-6}$alkyl is meant to include $C_{1-4}$alkyl and the higher homologues thereof having 5 or 6 carbon atoms such as, for example, pentyl, 2-methylbutyl, hexyl, 2-methylpentyl and the like; halo$C_{1-6}$alkyl is defined as polyhalosubstituted $C_{1-6}$alkyl, in particular $C_{1-6}$alkyl substituted with 1 to 6 halogen atoms, more in particular difluoro- or trifluoromethyl.

Het is meant to include all the possible isomeric forms of the heterocycles mentioned in the definition of Het, for instance, pyrrolyl includes 2H-pyrrolyl; triazolyl includes 1,2,4-triazolyl and 1,3,4-triazolyl; oxadiazolyl includes 1,2,3-oxadiazolyl, 1,2,4-oxadiazolyl, 1,2,5-oxadiazolyl and 1,3,4 oxadiazolyl; thiadiazolyl includes 1,2,3-thiadiazolyl, 1,2,4-thiadiazolyl, 1,2,5-thiadiazolyl and 1,3,4 thiadiazolyl; pyranyl includes 2H-pyranyl and 4H-pyranyl; thiazolopyridinyl includes thiazolo[5,4-b]pyridinyl, thiazolo[5,4-c]pyridinyl, thiazolo[5,4-d]pyridinyl and thiazolo[5,4-e]pyridinyl.

The heterocycles represented by Het may be attached to the remainder of the molecule of formula (I) through any ring carbon or heteroatom as appropriate. Thus, for example, when the heterocycle is imidazolyl, it may be a 1-imidazolyl, 2-imidazolyl, 4-imidazolyl and 5-imidazolyl; when it is triazolyl, it may be 1,2,4-triazol-1-yl, 1,2,4-triazol-3-yl, 1,2,4-triazol-5-yl, 1,3,4-triazol-1-yl and 1,3,4-triazol-2-yl; when it is benzthiazolyl, it may be 2-benzthiazolyl, 4-benzthiazolyl, 5-benzthiazolyl, 6-benzthiazolyl and 7-benzthiazolyl; when it is thiazolopyridinyl, it may be thiazolo[5,4-b]pyridin-2-yl, thiazolo[5,4-b]pyridin-4-yl, thiazolo[5,4-b]pyridin-5-yl, thiazolo[5,4-b]pyridin-6-yl, thiazolo[5,4-c]pyridin-2-yl, thiazolo[5,4-c]pyridin-4-yl, thiazolo[5,4-c]pyridin-5-yl, thiazolo[5,4-c]pyridin-7-yl, thiazolo[5,4-d]pyridin-2-yl, thiazolo[5,4-d]pyridin-4-yl, thiazolo[5,4-d]pyridin-6-yl, thiazolo[5,4-d]pyridin-7-yl, thiazolo[5,4-e]pyridin-2-yl, thiazolo[5,4-e]pyridin-5-yl, thiazolo[5,4-e]pyridin-6-yl and thiazolo[5,4-e]pyridin-7-yl.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (I) are able to form. Examples of such forms are e.g. hydrates, alcoholates and the like.

The N-oxide forms of the present compounds are meant to comprise the compounds of formula (I) wherein one or several nitrogen atoms are oxidized to the so-called N-oxide.

Some of the compounds of formula (I) may also exist in their tautomeric forms. Such forms although not explicitly indicated in the above formula are intended to be included within the scope of the present invention.

The term "stereochemically isomeric forms" as used hereinbefore defines all the possible stereoisomeric forms in which the compounds of formula (I) can exist. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration, used herein in accordance with Chemical Abstracts nomenclature. Stereochemically isomeric forms of the compounds of formula (I) are obviously intended to be embraced within the scope of this invention.

The compounds of formula (I) and some of the intermediates in the present invention contain one or more asymmetric carbon atoms. The pure and mixed stereochemically isomeric forms of the compounds of formula (I) are intended to be embraced within the scope of the present invention.

Whenever used hereinafter, the term "compounds of formula (I)" is meant to also include their N-oxide forms, their pharmaceutically acceptable addition salts, and their stereochemically isomeric forms.

The numbering of the phenyl ring bearing substituent $R^4$ is given hereinbelow and is used herein as such when indicating the position of the $R^4$ substituents on said phenyl ring, unless otherwise indicated.

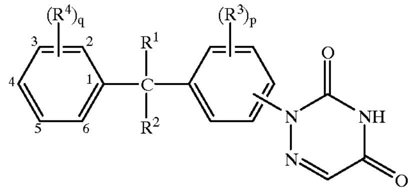

The carbon atom bearing the two phenyl rings and the $R^1$ and $R^2$ substituents will be referred herein as the central chiral carbon atom.

A suitable subgroup consists of those compounds of formula (I) or (I') wherein Het is other than pyrrolidinyl.

A special group of compounds are those compounds of formula (I) or (I') wherein $R^2$ is a radical of formula —C(═X)—Y—$R^5$ wherein Y is a direct bond and $R^5$ is Het.

Another special group of compounds are those compounds of formula (I) or (I') wherein $R^1$ is mono- or di($C_{1-6}$alkyl)amino$C_{1-6}$alkyloxy, mercapto, $C_{1-6}$alkylthio or $C_{1-6}$alkyl substituted with mono- or di($C_{1-6}$alkyl)amino, $C_{1-6}$alkyloxy or Het.

An interesting group of compounds are those compounds of formula (I) or (I') wherein the 6-azauracil moiety is connected to the phenyl ring in the para or meta position relative to the central chiral carbon atom, particularly in the para position.

Another interesting group of compounds are those compounds of formula (I) or (I') wherein $R^2$ is cyano.

Still another interesting group of compounds are those compounds of formula (1) or (I') wherein $R^2$ is a radical of formula —C(═X)—Y—$R^5$ wherein $R^5$ is hydrogen, $C_{1-6}$alkyl or aryl while Y is O, S or $NR^6$ wherein $R^6$ is hydrogen or $C_{1-6}$alkyloxy; or $R^5$ is aryl, $C_{1-6}$alkyl, halo, Het or $C_{1-6}$alkyl substituted with aryl while Y is a direct bond. Suitably, Het is optionally substituted piperazinyl, imidazolyl, thiazolyl or benzothiazolyl.

Yet another interesting group of compounds are those compounds of formula (I) or (I') wherein $R^1$ is hydrogen, aryl, $C_{1-6}$alkyl, mono- or di($C_{1-6}$alkyl)amino$C_{1-6}$alkyl or Het$C_{1-6}$alkyl.

Particular compounds are those compounds of formula (I) or (I') wherein $R^3$ and $R^4$ each independently are halo, halo$C_{1-6}$alkyl, hydroxy, $C_{1-6}$alkyl, $C_{1-6}$alkyloxy, $C_{1-6}$alkylcarbonyloxy or aryl, more in particular, bromo, chloro, fluoro, trifluoromethyl, methyl, hydroxy, methoxy, methylcarbonyloxy or phenyl.

Other particular compounds are those compounds of formula (I) or (I') wherein p is 0, 1 or 2, and q is 0, 1, 2 or 3, more in particular, p and q each independently are 1 or 2.

Preferred compounds are those compounds of formula (I) or (I') wherein q is 1 or 2 and one $R^4$ substituent, preferably selected from chloro, fluoro, methyl, hydroxy, methoxy, methylcarbonyloxy and phenyl, is in the 4 position.

Other preferred compounds are those compounds of formula (I) or (I') wherein p is 1 or 2 and the one or two $R^3$ substituents, preferably selected from bromo, chloro, methyl, methoxy or trifluoromethyl, are in the ortho position relative to the central chiral carbon atom.

More preferred compounds are those compounds of formula (I) or (I') wherein the 6-azauracil moiety is in the para position relative to the central chiral carbon atom; p is 1 or 2 and one $R^3$ substituent is chloro positioned ortho relative to the central chiral carbon atom; q is 1 or 2 and one $R^4$ substituent is chloro in the 4 position.

Particularly preferred compounds are those compounds as described hereinabove as more preferred compounds wherein $R^2$ is cyano or a radical of formula —C(=X)—Y—$R^5$ wherein Y is a direct bond.

The compounds of the present invention can generally be prepared as described in U.S. Pat. Nos. 4,631,278 and 4,767,760.

In particular, the compounds of formula (I') can be prepared by cyclizing an intermediate of formula (II) and eliminating the group E from the thus obtained dione of formula (III).

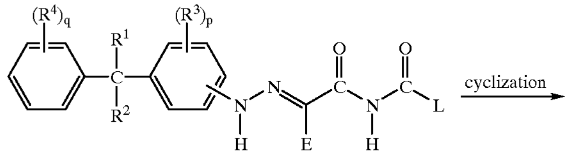

(II)

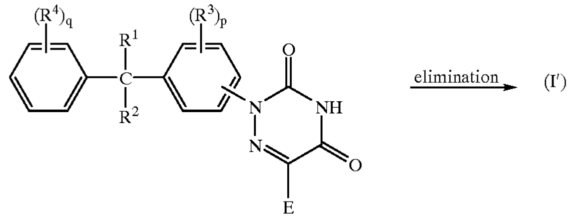

(III)

A suitable way of eliminating group E, which is for example a carboxyl group, may be reacting intermediate of formula (III) with mercaptoacetic acid or a functional derivative thereof.

The compounds of formula (I') may also be prepared by eliminating the protective group P in the intermediates of formula (IV).

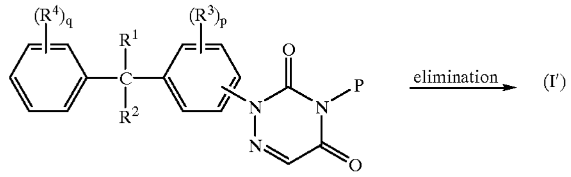

(IV)

A suitable way of eliminating group P, which is for example a alkyloxyalkyloxyalkyl moiety, may be reacting intermediate of formula (IV) with a acid or an acid mixture such as hydrochloric acid, acetic acid or a mixture thereof. Alternatively, the protective group P may be removed by reacting an intermediate of formula (IV) with a suitable reagent such as, for example, boron tribromide, in a reaction-inert solvent such as, for example, dichloromethane.

The compounds of formula (I') wherein $R^2$ is cyano, said compounds being represented by formula (I'-a), can be prepared by converting the hydroxyl function of an intermediate of formula (V) into a suitable leaving group W such as, for example, a halogen or a sulfonyloxy group, and subsequently converting said leaving group W in the thus formed intermediate of formula (VI) into a nitrile function.

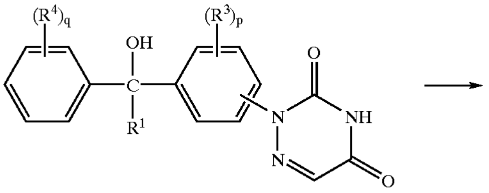

(III)

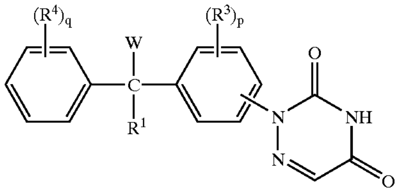

(VI)

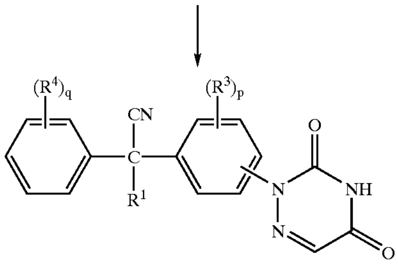

(I'-a)

The compounds of formula (I') wherein $R^1$ is hydrogen and $R^2$ is cyano, said compounds being represented by formula (I'-a-1), can be prepared by reacting the carbonyl group in the intermediates of formula (VII) with a suitable reagent such as, for example, 1-[(isocyanomethyl)sulfonyl]-4-methylbenzene or a functional derivative thereof.

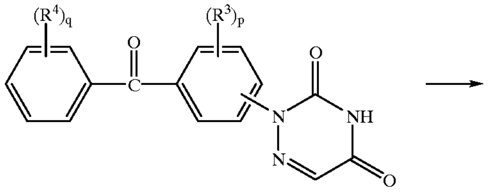

(VII)

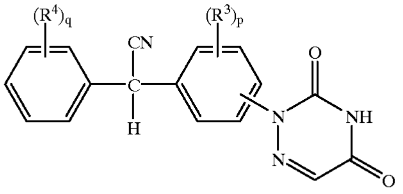

(I'-a-1)

The compounds of formula (I) can be converted into each other following art-known procedures of functional group transformation and are described in U.S. Pat. No. 4,767,760, Some interesting group transformation reactions described therein are mentioned hereinafter.

In order to simplify the structural representation of the compounds of formula (I'), the group

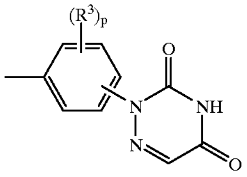

will hereinafter be represented by the symbol D.

The compounds of formula (I'-a) may be partially or completely hydrolyzed, thus yielding compounds of formula (I') wherein $R^2$ is an aminocarbonyl or a carboxyl group, the former being represented by formula (I'-f), the latter by (I'-b). The compounds of formula (I'-f) can further be hydrolized to compounds of formula (I'-b).

The compounds of formula (I'-a) may also be converted to compounds of formula (I'-g) wherein $R^2$ is an aminothioxomethyl group.

The acids of formula (I'-b) can be converted to the corresponding acylhalides of formula (I'-c). Said acylhalides of formula (I'-c) can further be derivatized using $HN(R^5)(R^6)$ to the corresponding amides of formula (I'-d) which in turn may further be reacted to a heteroaryl ketone of formula (I'-e) using a suitable metal alkyl such as, for example, butyl lithium, in a reaction-inert solvens such as, for example, tetrahydrofuran, hexane, diethylether or a mixture thereof. The latter reaction may conveniently be performed under an inert atmosphere such as, for example, oxygen-free nitrogen, and at a low reaction temperature, preferably at about −70° C. The acylhalides of formula (I'-c) can also be reacted with a Grignard reagent, e.g. RMgX, wherein X is a suitable counter ion such as a halogen, and R is $C_{3-7}$cycloalkyl or $C_{1-6}$alkyl optionally substituted with aryl or Het, thus obtaining intermediates of formula (I'-h).

priate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I') may be obtained by the application of art-known procedures. Diastereomers may be separated by physical methods such as selective crystallization and chromatographic techniques, e.g. counter-current distribution, liquid chromatography and the like.

The compounds of formula (I') as prepared in the hereinabove described processes are generally racemic mixtures of enantiomers which can be separated from one another following art-known resolution procedures. The racemic compounds of formula (I') which are sufficiently basic or acidic may be converted into the corresponding diastereomeric salt forms by reaction with a suitable chiral acid respectively with a suitable chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I') involves liquid chromatography using a chiral stationary phase. Said pure stereochemically isomeric forms may also be derived from the corresponding pure stereochemically isomeric forms of the appropriate starting materials, provided that the reaction occurs stereospecifi-

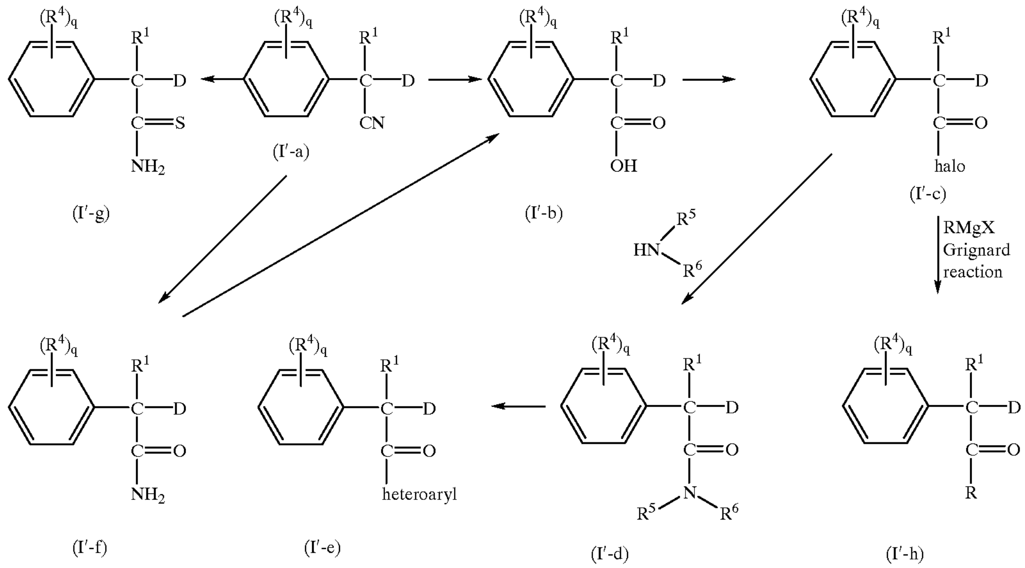

In addition, the compounds of formula (I') may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Approcally. Preferably if a specific stereoisomer is desired, said compound will be synthesized by stereospecific methods of preparation. These methods will advantageously employ enantiomerically pure starting materials.

An alternative manner of separating the enantiomeric forms of the compounds of formula (I) and intermediates involves liquid chromatography, in particular liquid chromatography using a chiral stationary phase.

A number of intermediates and starting materials in the foregoing preparations are commercially available or are known compounds which may be prepared according to art-known methodologies of preparing said or similar intermediates. In particular, the preparation of the intermediates of formula (II), (IV), (V) and (VII) are described in U.S. Pat. Nos. 4,631,278, 4,767,760, 3,883,527 and Carroll et al. in J. Med. Chem. 1983, 26, 96–100.

IL-5, also known as eosinophil differentiating factor (EDF) or eosinophil colony stimulating factor (Eo-CSF), is a major survival and differentiation factor for eosinophils and basophils and therefore thought to be a key player in eosinophil infiltration into tissues. There is ample evidence that eosinophil influx is an important pathogenic event in bronchial asthma and allergic diseases such as, cheilitis, irritable bowel disease, eczema, urticaria, vasculitis, vulvitis, winterfeet, atopic dermatitis, pollinosis, allergic rhinitis and allergic conjunctivitis; and other inflammatory diseases, such as eosinophilic syndrome, allergic angiitis, eosinophilic fasciitis, eosinophilic pneumonia, PIE syndrome, idiopathic eosinophilia, eosinophilic myalgia, Crohn's disease, ulcerative colitis and the like diseases.

The present compounds also inhibit the production of other chemokines such as monocyte chemotactic protein-1 and -3 (MCP-1 and MCP-3). MCP-1 is known to attract both T-cells, in which IL-5 production mainly occurs, and monocytes, which are known to act synergetically with eosinophils (Carr et al., 1994, Immunology, 91, 3652–3656). MCP-3 also plays a primary role in allergic inflammation as it is known to mobilize and activate basophil and eosinophil leukocytes (Baggiolini et al., 1994, immunology Today, 15(3), 127–133).

The present compounds have no or little effect on the production of other chemokines such as IL-1, IL-2, IL-3, IL-4, IL-6, IL-10, γ-interferon (IFN-γ) and granulocyte-macrophage colony stimulating factor (GM-CSF) indicating that the present IL-5 inhibitors do not act as broad-spectrum immunosuppressives.

The selective chemokine inhibitory effect of the present compounds can be demonstrated by in vitro chemokine measurements in human blood of which the test results for IL-5 are presented in the experimental part hereinafter. In vivo observations such as the inhibition of eosinophilia in mouse ear, the inhibition of blood eosinophilia in the Ascaris mouse model; the reduction of serum IL-5 protein production and splenic IL-5 mRNA expression induced by anti-CD3 antibody in mice and the inhibition of allergen- or Sephadex-induced pulmonary influx of eosinophils in guinea-pig are indicative for the usefulness of the present compounds in the treatment of eosinophil-dependent inflammatory diseases.

The present inhibitors of IL-5 production are orally active compounds.

In view of the above pharmacological properties, the present compounds can be used in the manufacture of a medicament for treating eosinophil-dependent inflammatory diseases as mentioned hereinabove, in particular bronchial asthma, atopic dermatitis, allergic rhinitis and allergic conjunctivitis. The present invention also involves two groups of novel compounds for use as a medicine. One of said groups consists of those compounds of formula (I') wherein $R^1$ is mono- or di($C_{1-6}$alkyl)amino$C_{1-6}$alkyloxy, mercapto, $C_{1-6}$alkylthio or $C_{1-6}$alkyl substituted with mono- or di($C_{1-6}$ alkyl)amino, $C_{1-6}$alkyloxy or Het, the other group consists of those compounds of formula (I') wherein $R^2$ is a radical of formula —C(=X)—Y—$R^5$ wherein Y is a direct bond and $R^5$ is Het.

In view of the utility of the compounds of formula (I), there is provided a method of treating warm-blooded animals, including humans, suffering from eosinophil-dependent inflammatory diseases, in particular bronchial asthma, atopic dermatitis, allergic rhinitis and allergic conjunctivitis. Said method comprises the systemic or topical administration of an effective amount of a compound of formula (I), a N-oxide form, a pharmaceutically acceptable addition salt or a possible stereoisomeric form thereof, to warm-blooded animals, including humans.

The present invention also provides compositions for treating eosinophil-dependent inflammatory diseases comprising a therapeutically effective amount of a compound of formula (I) and a pharmaceutically acceptable carrier or diluent together with instructions for the use thereof for the treatment of an eosinophil-dependent inflammatory disease.

In particular, the present invention provides compositions for treating eosinophil-dependent inflammatory diseases comprising a therapeutically effective amount of a compound of formula (I') wherein $R^2$ is a radical of formula —C(=X)—Y—$R^5$ wherein Y is a direct bond and $R^5$ is Het or a compound of formula (I') wherein $R^1$ is mono- or di($C_{1-6}$alkyl)amino$C_{1-6}$alkyloxy, mercapto, $C_{1-6}$alkylthio or $C_{1-6}$alkyl substituted with mono- or di($C_{1-6}$alkyl)amino, $C_{1-6}$alkyloxy or Het, and a pharmaceutically acceptable carrier or diluent.

To prepare the aforementioned pharmaceutical compositions, a therapeutically effective amount of the particular compound, optionally in addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous, or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. As appropriate compositions for topical application there may be cited all compositions usually employed for topically administering drugs e.g. creams, gellies, dressings, shampoos, tinctures, pastes, ointments, salves, powders and the like. Application of said compositions may be by aerosol, e.g. with a propellent such as nitrogen, carbon dioxide, a freon, or without a propellent such as a pump spray, drops, lotions, or a semisolid such as a thickened composition which can be applied by a swab. In particular, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Preferred compositions are those compositions containing a novel compound of formula (I') wherein $R^2$ is a radical of formula —C(=X)—Y—$R^5$ wherein Y is a direct bond and $R^5$ is Het, or a novel compound of formula (I') wherein $R^1$ is mono- or di($C_{1-6}$alkyl)amino-$C_{1-6}$alkyloxy, mercapto, $C_{1-6}$alkylthio or $C_{1-6}$alkyl substituted with mono- or di($C_{1-6}$ alkyl)amino, $C_{1-6}$alkyloxy or Het, and are in dosage unit form, comprising per dosage unit an effective quantity of active ingredient in admixture with suitable carriers.

In order to enhance the solubility and/or the stability of the compounds of formula (I) in pharmaceutical compositions, it can be advantageous to employ α-, β- or γ-cyclodextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkylcarbonyl, particularly acetyl; $C_{1-6}$alkyloxycarbonyl$C_{1-6}$alkyl or carboxy-$C_{1-6}$ alkyloxy$C_{1-6}$alkyl, particularly carboxymethoxypropyl or carboxyethoxypropyl; $C_{1-6}$alkylcarbonyloxy$C_{1-6}$alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

Due to their high degree of selectivity as IL-5 inhibitors, the compounds of formula (I) as defined above, are also useful to mark or identify receptors. To this purpose, the compounds of the present invention need to be labelled, in particular by replacing, partially or completely, one or more atoms in the molecule by their radioactive isotopes. Examples of interesting labelled compounds are those compounds having at least one halo which is a radioactive isotope of iodine, bromine or fluorine; or those compounds having at least one $^{11}C$-atom or tritium atom.

One particular group consists of those compounds of formula (I) wherein $R^3$ and/or $R^4$ are a radioactive halogen atom. In principle, any compound of formula (I) containing a halogen atom is prone for radiolabelling by replacing the halogen atom by a suitable isotope. Suitable halogen radioisotopes to this purpose are radioactive iodides, e.g. $^{122}I$, $^{123}I$, $^{125}I$, $^{131}I$; radioactive bromides, e.g. $^{75}Br$, $^{76}Br$, $^{77}Br$ and $^{82}Br$, and radioactive fluorides, e.g. $^{18}F$. The introduction of a radioactive halogen atom can be performed by a suitable exchange reaction or by using any one of the procedures as described hereinabove to prepare halogen derivatives of formula (I).

Another interesting form of radiolabelling is by substituting a carbon atom by a $^{11}C$-atom or the substitution of a hydrogen atom by a tritium atom.

Hence, said radiolabelled compounds of formula (I) can be used in a process of specifically marking receptor sites in biological material. Said process comprises the steps of (a) radiolabelling a compound of formula (I), (b) administering this radiolabelled compound to biological material and subsequently (c) detecting the emissions from the radiolabelled compound. The term biological material is meant to comprise every kind of material which has a biological origin. More in particular this term refers to tissue samples, plasma or body fluids but also to animals, specially warm-blooded animals, or parts of animals such as organs.

The radiolabelled compounds of formula (I) are also useful as agents for screening whether a test compound has the ability to occupy or bind to a particular receptor site. The degree to which a test compound will displace a compound of formula (I) from such a particular receptor site will show the test compound ability as either an agonist, an antagonist or a mixed agonist/antagonist of said receptor.

When used in in vivo assays, the radiolabelled compounds are administered in an appropriate composition to an animal and the location of said radiolabelled compounds is detected using imaging techniques, such as, for instance, Single Photon Emission Computerized Tomography (SPECT) or Positron Emission Tomography (PET) and the like. In this manner the distribution of the particular receptor sites throughout the body can be detected and organs containing said receptor sites can be visualized by the imaging techniques mentioned hereinabove. This process of imaging an organ by administering a radiolabelled compound of formula (I) and detecting the emissions from the radioactive compound also constitutes a part of the present invention.

A suitable therapeutically effective daily amount would be from 0.01 mg/kg to 50 mg/kg body weight, in particular from 0.05 mg/kg to 10 mg/kg body weight. A method of treatment may also include administering the active ingredient on a regimen of between two or four intakes per day.

EXPERIMENTAL PART

A. Preparation of the Intermediate Compounds

Herinafter, "THF" stands for tetrahydrofuran, "RT" stands for room temperature, "DIPE" stands for diisopropylether, "EtOAc" stands for ethylacetate and "DMF" stands for N,N-dimethylformamide.

Example A.1 a) A solution of 4-chloro-3-(trifluoromethyl)benzeneacetonitrile (0.114 mol) in THF (100 ml) was added dropwise at RT to a solution of 1,2,3-trichloro-5-nitrobenzene (0.114 mol) and N,N,N-triethylbenzenemethanaminium chloride (3 g) in NaOH (150 ml) and THF (100 ml). The mixture was stirred at RT for 2 hours, then poured out on ice, acidified with a concentrated HCl solution and extracted with $CH_2Cl_2$. The organic layer was separated, dried, filtered and the solvent was evaporated. The residue was crystallized from DIPE. The precipitate was filtered off and dried, yielding 40.4 g (86.5%) of (±)-2,6-dichloro-α-[4-chloro-3-(trifluoromethyl) phenyl]-4-nitrobenzene-acetonitrile (interm. 1).

b) A mixture of (3,4-dichlorophenyl)acetonitrile (0.149 mol) in DMF (100 ml) was stirred at 0° C. under $N_2$ flow. Sodium hydride (0.223 mol) was added portionwise. The mixture was stirred at 0° C. under $N_2$ flow for 1 hour. A mixture of, 2-methoxy-1,3-dimethyl-5-nitrobenzene (0.149 mol) in DMF (100 ml) was added dropwise at 0° C. under $N_2$ flow. The mixture was stirred at RT for 6 hours, then cooled, hydrolized with $H_2O$ and with HCl 3N and extracted with EtOAc. The organic layer was separated, washed several times with $H_2O$, dried, filtered and the solvent was evaporated. The residue was crystallized from DIPE. The precipitate was filtered off and dried, yielding 43.4 g (87%) of (±)-α-(3,4-dichlorophenyl)-2,6-dimethyl-4-nitrobenzeneacetonitrile (interm. 48).

c) A solution of intermediate 1 (0.0466 mol), iodomethane (0.0606 mol), KOH (0.1864 mol) and N,N,N-triethylbenzenemethanaminium chloride (0.0466 mol) in toluene (200 ml) was stirred at 50° C. for 2 hours. The mixture was poured out into water, acidified with HCl (3N) and extracted with $CH_2Cl_2$. The organic layer was separated, dried, filtered and the solvent was evaporated. The residue was purified by column chromatography over silica gel (eluent: cyclohexane/EtOAc 90/10). The pure fractions were collected and the solvent was evaporated, yielding 11 g (55%) of (±)-2,6-dichloro-α-[4-chloro-3-(trifluoromethyl) phenyl]-(X-methyl-4-nitrobenzene-acetonitrile (interm. 2)

Example A.2 a) A mixture of intermediate 2 (0.0259 mol) in methanol (200 ml) was hydrogenated at 40° C. overnight with platinum-on-activated carbon (1%; 1 g) as a catalyst in the presence of thiophene (10% in ethanol; 1 ml). After uptake of hydrogen, the catalyst was filtered through celite, washed with $CH_3OH$ and the filtrate was evaporated, yielding 10 g (98%) of (±)-4-amino-2,6-dichloro-α-[4-chloro-3-(trifluoromethyl)-phenyl]-α-methylbenzeneacetonitrile (interm. 3).

b) A mixture of intermediate 1 (0.138 mol) in methanol (300 ml) was hydrogenated at RT under a 3 bar pressure for 1 hour with Raney Nickel (50 g) as a catalyst in the presence of a 10% thiophene solution in ethanol (5 ml). After uptake of hydrogen, the catalyst was filtered through celite, washed with $CH_3OH$ and $CH_2Cl_2$ and the filtrate was evaporated, yielding 49.5 g (94%) of (±)-4-amino-2,6-dichloro-α-[4-chloro-3-(trifluoromethyl)phenyl]benzeneacetonitrile (interm. 46).

c) A solution of 15% $TiCl_3$ in water (0.13 mol) was added dropwise at RT to a solution of (±)-2,6-dibromo-α-(4-chlorophenyl)-4-nitrobenzeneacetonitrile (0.026 mol) in THF (200 ml). The mixture was stirred at RT for 2 hours, poured out into $H_2O$ and extracted with $CH_2Cl_2$. The organic layer was separated, washed with $H_2O$ and with $K_2CO_3$ 10%, dried, filtered and the solvent was evaporated. A part of this residue (2 g) was crystallized from diethyl ether. The precipitate was filtered off and dried, yielding 1.3 g (±)-4-amino-2,6-dibromo-α-(4-chlorophenyl) benzeneacetonitrile (interm. 47).

Example A.3 a) A solution of sodium nitrite (0.0243 mol) in water (10 ml) was added dropwise at 5° C. to a solution of intermediate 3 (0.0243 mol) in acetic acid (75 ml) and concentrated HCl (20 ml). The mixture was stirred at 0° C. for 35 minutes and then added dropwise to a solution of ethyl (cyanoacetyl) carbamoate (0.0326 mol) and sodium acetate (112 g) in ice water (1300 ml). The mixture was stirred at 0° C. for 45 minutes. The precipitate was filtered off, washed with water and taken up in $CH_2Cl_2$. The organic layer was separated, washed with water, dried, filtered and the solvent was evaporated, yielding 15.2 g (±)-ethyl 2-cyano-2-[[3,5-dichloro-4-[1-[4-chloro-3-(trifluoromethyl)phenyl]-1-cyanoethyl]phenyl]hydrazono]-1-oxoethylcarbamate (interm. 4)

b) A mixture of intermediate 4 (0.0271 mol) and potassium acetate (0.0285 mol) in acetic acid (150 ml) was stirred and refluxed for 3 hours and then poured out on ice. The precipitate was filtered off, washed with water and taken up in EtOAc. The organic layer was separated, washed with water, dried, filtered and the solvent was evaporated, yielding 12 g (86%) of (±)-2-[3,5-dichloro-4-[1-[4-chloro-3-(trifluoromethyl)phenyl]-1-cyanoethyl]phenyl]-2,3,4,5-tetrahydro-3,5-dioxo-1,2,4-triazine-6-carbonitrile (interm. 5).

c) A mixture of intermediate 5 (0.0223 mol) in HCl (40 ml) and acetic acid (150 ml) was stirred and refluxed for 3 hours and then poured out into ice water. The precipitate was filtered off, taken up in $CH_2Cl_2$ and $CH_3OH$, washed with water, dried, filtered and the solvent was evaporated, yielding 11.4 g (96%) of (±)-2-[3,5-dichloro-4-[1-[4-chloro-3-trifluoromethyl)phenyl]-1-cyanoethyl]phenyl]-2,3,4,5-tetrahydro-3,5-dioxo-1,2,4-triazine-6-carboxylic acid (interm. 6).

The following intermediates were prepared according to the procedures described in example A.3.

TABLE 1

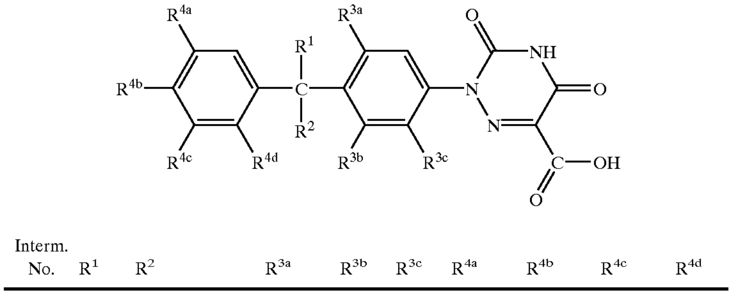

| Interm. No. | $R^1$ | $R^2$ | $R^{3a}$ | $R^{3b}$ | $R^{3c}$ | $R^{4a}$ | $R^{4b}$ | $R^{4c}$ | $R^{4d}$ |
|---|---|---|---|---|---|---|---|---|---|
| 7 | $CH_3$ | CN | Cl | H | H | H | Cl | Cl | H |
| 8 | $CH_3$ | CN | Cl | H | H | H | $OCH_3$ | $OCH_3$ | H |

TABLE 1-continued

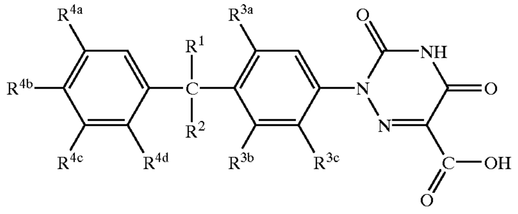

| Interm. No. | $R^1$ | $R^2$ | $R^{3a}$ | $R^{3b}$ | $R^{3c}$ | $R^{4a}$ | $R^{4b}$ | $R^{4c}$ | $R^{4d}$ |
|---|---|---|---|---|---|---|---|---|---|
| 9 | $CH_3$ | CN | Cl | H | H | H | $OCH_3$ H | H | |
| 10 | $CH_3$ | CN | Cl | H | H | H | Cl | $OCH_3$ | H |
| 11 | $CH_3$ | CN | Cl | H | $CH_3$ | H | Cl | $CF_3$ | H |
| 12 | $CH_3$ | CN | Cl | H | H | H | Cl | $OCH_3$ | H |
| 13 | $CH_3$ | CN | $OCH_3$ | H | H | H | Cl | $CF_3$ | H |
| 14 | $CH_3$ | CN | Cl | H | H | $OCH_3$ | $OCH_3$ | $OCH_3$ | H |
| 15 | $CH_3$ | CN | Cl | Cl | H | H | Cl | Cl | H |
| 16 | $CH_3$ | CN | Cl | H | H | H | Cl | $CH_3$ | H |
| 17 | $CH_3$ | CN | Cl | H | H | H | $CH_3$ | $OCH_3$ | H |
| 18 | $CH_3$ | CN | Cl | H | H | H | Cl | H | Cl |
| 19 | $CH_3$ | CN | H | H | H | H | Cl | H | Cl |
| 20 | $CH_3$ | CN | $CH_3$ | H | H | $CF_3$ | Cl | H | H |
| 21 | $CH_3$ | CN | Cl | H | H | H | phenyl | H | H |
| 33 | H | CN | $CH_3$ | $CH_3$ | H | H | Cl | Cl | H |
| 34 | H | CN | Cl | Cl | H | H | Cl | $CH_3$ | H |
| 35 | $CH_3$ | CN | Cl | Cl | H | H | Cl | F | H |
| 36 | H | CN | Cl | Cl | H | H | Cl | $OCH_3$ | H |
| 37 | H | CN | Br | Br | H | H | Cl | H | H |
| 38 | $CH_3$ | $C(=O)OC_2H_5$ | Cl | Cl | H | H | Cl | H | H |

Example A.4 a) A mixture of (±)-4-chloro-α-[2-chloro-3-(4,5-dihydro-3,5-dioxo-1,2,4-triazin-2(3H)-yl)phenyl]-3-(trifluoromethyl)benzeneacetonitrile (0.00542 mol), 1-(chloromethoxy)-2-methoxyethane (0.006 mol) and triethylamine (0.0065 mol) in THF (15 ml) was stirred at RT for 2 hours. The mixture was poured out into water and extracted with EtOAc. The organic layer was separated, dried, filtered and the solvent was evaporated, yielding 3.4 g of (±)-4-chloro-α-[2-chloro-3-[4,5-dihydro-4-[(2-methoxyethoxy)methyl]-3,5-dioxo-1,2,4-triazin-2(3H)-yl]phenyl]-3-(trifluoromethyl)benzeneacetonitrile (interm. 22).

(±)-2-chloro-α-(4-chlorophenyl)-4-[4,5-dihydro-4-[(2-methoxyethoxy)methyl]-3,5-dioxo-1,2,4-triazin-2(3H)-yl]benzeneacetonitrile was prepared in an analogous way (interm. 39).

b) 2-methyl-2-propanol, potassium salt (0.0193 mol) was added portionwise at 0° C. under $N_2$ flow to a solution of intermediate 22 (0.00642 mol) and iodomethane (0.0321 mol) in DMF (10 ml). The mixture was stirred at 0° C. for 2 hours, then poured out into ice water and extracted with diethyl ether. The organic layer was separated, washed with water, dried, filtered and the solvent was evaporated. The residue was purified by column chromatography over silica gel (eluent: cyclohexane/EtOAc 50/50 to 35/65). The pure fractions were collected and the solvent was evaporated, yielding 2.07 g (60%) of (±)-4-chloro-α-[2-chloro-3-[4,5-dihydro-4-[(2-methoxyethoxy)methyl]-3,5-dioxo-1,2,4-triazin-2(3H)-yl]phenyl]-α-methyl-3-(trifluoromethyl)benzeneacetonitrile (interm. 23).

(±)-4-chloro-α-[2-chloro-5-[4,5-dihydro-4-[(2-methoxyethoxy)methyl]-3,5-dioxo-1,2,4-triazin-2(3H)-yl]phenyl]-α-methyl-3-(trifluoromethyl)benzeneacetonitrile was prepared in an analogous way (interm. 24).

Example A.5 a) A solution of 4-bromo-1-chloro-2-(trifluoromethyl)benzene (0.165 mol) in THF (30 ml) was added dropwise under $N_2$ flow to a suspension of Mg (0.181 mol) and a crystal of $I_2$ in THF (20 ml). The mixture was stirred at 30–35° C. for 2.5 hours and then cooled to 10° C. The mixture was added dropwise at 5° C. under $N_2$ flow to a solution of N-(2-chloro-3-formylphenyl)acetamide (0.0788 mol) in THF (500 ml). The mixture was stirred at RT for 3 hours, poured out into ice and $NH_4Cl$, and extracted with EtOAc. The organic layer was separated, dried, filtered and the solvent was evaporated. The residue was purified by column chromatography (eluent: $CH_2Cl_2/CH_3OH$ 98.5/1.5). The pure fractions were collected and the solvent was evaporated, yielding 22.2 g (74%) of (±)-N-[2-chloro-3-[[4-chloro-3-(trifluoromethyl)phenyl]hydroxymethyl]phenyl]acetamide (interm. 25).

b) A mixture of intermediate 25 (0.0587 mol) and manganese(IV) oxide (0.587 mol) in $CH_2Cl_2$ (400 ml) was stirred at RT for 24 hours and filtered over celite. The solvent was evaporated, yielding 19.21 g (87%) of N-[2-chloro-3-[4-chloro-3-(trifluoromethyl)benzoyl]phenyl]acetamide (interm. 26).

c) A mixture of intermediate 26 (0.0511 mol) in HCl (6N; 200 ml) was stirred and refluxed for 5 hours. The mixture was cooled, poured into ice, basified with $NH_4OH$ and extracted with $CH_2Cl_2$. The organic layer was dried, filtered and the solvent was evaporated, yielding 17.1 g (100%) of (3-amino-2-chlorophenyl)[4-chloro-3-(trifluoromethyl)phenyl]methanone (interm. 27).

d) 2-[2-chloro-3-[4-chloro-3-(trifluoromethyl)benzoyl]phenyl]-2,3,4,5-tetrahydro-3,5-dioxo-1,2,4-triazine-6-carboxylic acid was prepared according to the procedures described in example A2.a), A2.b) and A2.c) (intern. 28).

e) A mixture of intermediate 28 (0.0207 mol) in mercaptoacetic acid (10 ml) was heated at 160° C. for 3 hours. The solution was cooled and poured on ice. EtOAc was added and the mixture was basified with $NaHCO_3$. The organic layer was separated, dried, filtered and the solvent was evaporated. 0.8 g of the residue was crystallized from 2-propanol/DIPE. The precipitate was filtered off and dried, yielding 0.5 g (93%) of 2-[2-chloro-3-[4-chloro-3-(trifluoromethyl)benzoyl]phenyl]-1,2,4-triazine-3,5(2H, 4H)-dione (interm. 29).

2-[4-chloro-3-[4-chloro-3-(trifluoromethyl)benzoyl] phenyl]-1,2,4-triazine-3,5(2H,4H)-dione was prepared according to the procedures described in example A5.a) through A5.e) (interm. 30).

Example A.6 a) A mixture of 2-[4-(4-chlorobenzoyl)phenyl]-1,2,4-triazine-3,5-(2H,4H)-dione (0.05 mol), ethanol (150 ml), water (150 ml) and NaOH (50%; 10 ml) was stirred at 10° C. A mixture of $NaBH_4$ (0.05 mol), water (50 ml) and NaOH (50%; 2 ml) was added dropwise during 15 minutes. After stirring for 3 hours, 300 ml ice was added. The mixture was acidified with concentrated HCl. The product was extracted with $CHCl_3$, yielding 5.8 g of 2-[4-[(4-chlorophenyl) hydroxymethyl]phenyl]-1,2,4-triazine-3,5-(2H,4H)-dione (intern. 31). The organic layer was dried, filtered and evaporated. The residue was crystallized with 2-propanol. The product was filtered off, washed with 2,2'-oxybispropane and dried, yielding a second fraction of 5.5 g of intermediate 31.

b) A mixture of intermediate 31 (0.053 mol), thionylchloride (50 ml) and $CHCl_3$ (200 ml) was stirred and refluxed for 2 hours. The solvent was evaporated. After the addition of toluene, the solvent was evaporated again, yielding 18.4 g of 2-[4-[chloro(4-chlorophenyl)methyl]phenyl]-1,2,4-triazine-3,5-(2H,4H)-dione (interm. 32).

Example A.7 a) NaH (0.042 mol; 80% in oil) was added portionwise at 10° C. under $N_2$ flow to a solution of intermediate 39 (0.0325 mol) in DMF (90 ml). The mixture was stirred for 15 minutes. A solution of 1-bromo-3-chloro-propane (0.065 mol) in DMF (20 ml) was added dropwise. The mixture was stirred at RT for 24 hours. $H_2O$ (250 ml) was added. The mixture was filtered over celite, washed with $H_2O$ and extracted with $CH_2Cl_2$. The organic layer was separated, dried, filtered and the solvent was evaporated. The residue was purified by column chromatography over silica gel (eluent: $CH_2Cl_2$/EtOAc 85/15). The pure fractions were collected and the solvent was evaporated, yielding 7.5 g (43%) of (±)-2-chloro-α-(4-chlorophenyl)-α-(3-chloropropyl)-4-[4,5-dihydro-4-[(2-methoxyethoxy) methyl]-3,5-dioxo-1,2,4-triazin-2(3H)-yl] benzeneacetonitrile (interm. 40).

b) A mixture of intermediate 40 (0.0132 mol), dimethylamine (0.066 mol) and potassium carbonate (0.066 mol) in acetonitrile (100 ml) was stirred and refluxed for 12 hours and then allowed to cool to RT. $H_2O$ was added. The mixture was extracted with $CH_2Cl_2$. The organic layer was separated, dried, filtered and the solvent was evaporated. The residue was purified by column chromatography over silica gel (eluent: $CH_2Cl_2/CH_3OH/NH_4OH$ 97.5/2.5/0.5). The pure fractions were collected and the solvent was evaporated, yielding 2.5 g (35%) of (±)-2-chloro-α-(4-chlorophenyl)-4-[4,5-dihydro-4-[(2-methoxyethoxy) methyl]-3,5-dioxo-1,2,4-triazin-2(3H)-yl]-α-[3-(dimethylamino)propyl]-benzeneacetonitrile (interm. 41).

Example A.8 a) A mixture of (±)-4-amino-2,6-dichloro-α-[4-chloro-3-(trifluoromethyl)phenyl]-α-methylbenzeneacetonitrile (0.08 mol) in acetic acid (250 ml) and concentrated chloric acid (0.24 mol) was stirred at ±10° C. A solution of sodium nitrite (0.08 mol) in water (15 ml) was added dropwise over 30 minutes at ±10° C. The mixture was stirred for one hour. Sodium acetate (0.24 mol) and carbamic acid, (1,3-dioxo-1,3-propanediyl)bis-, diethyl ester (0.088 mol) were added in one portion. The resulting reaction mixture was stirred for 2 hours at RT. The mixture was poured out into ice-water, and the resulting precipitate was filtered off, washed with water, then dissolved in $CH_2Cl_2$. The organic solution was dried, filtered and the solvent evaporated. A sample of the residue (2 g) was purified over silica gel on a glass filter (eluent: $CH_2Cl_2/CH_3OH$ 99/1). The desired fractions were collected and the solvent was evaporated. The residue was stirred in DIPE, filtered off, washed and dried, yielding 0.95 g of diethyl (A)-N,N'-[2-[[3,5-dichloro-4-[1-[4-chloro-3-(trifluoromethyl)phenyl]-1-cyanoethyl]phenyl]hydrazono]-1,3-dioxo-1,3-propanediyl]dicarbamate (interm. 42; $[\alpha]_{20}^{D}$=+37.83° @ 20.3 mg/2 ml in methanol).

b) A solution of intermediate 42 (0.08 mol) and potassium acetate (0.08 mol) in acetic acid (350 ml) was stirred and refluxed for 4 hours. The solvent was evaporated, yielding ethyl (A)-[[2-[3,5-dichloro-4-[1-[4-chloro-3-(trifluoromethyl)phenyl]-1-cyanoethyl]phenyl]-2,3,4,5-tetrahydro-3,5-dioxo-1,2,4-triazin-6-yl]carbonyl]carbamate (interm. 43).

c) A solution of intermediate 43 (0.08 mol) in concentrated chloric acid (100 ml) and acetic acid (350 ml) was stirred and refluxed overnight. The reaction mixture was poured out into ice-water, and the resulting precipitate was filtered off, washed with water, then dissolved in $CH_2Cl_2/CH_3OH$ 98/2. The organic solution was dried, filtered and the solvent was evaporated, yielding (A)-2-[3,5-dichloro-4-[1-[4-chloro-3-(trifluoromethyl)phenyl]-1-cyanoethyl] phenyl]-2,3,4,5-tetrahydro-3,5-dioxo-1,2,4-triazine-6-carboxylic acid (interm. 44; $[\alpha]_{20}^{D}$=+33.76° @ 20.38 mg/2 ml in methanol).

(B)-2-[3,5-dichloro-4-[1-[4-chloro-3-(trifluoromethyl) phenyl]-1-cyanoethyl]phenyl]-2,3,4,5-tetrahydro-3,5-dioxo-1,2,4-triazine-6-carboxylic acid was prepared in an analogous way (interm. 45).

B. Preparation of the Final Compounds

Example B.1

A mixture of intermediate 6 (0.044 mol) in mercaptoacetic acid (23 ml) was stirred at 175° C. for 2 hours. The mixture was cooled, poured out on ice, basified with $K_2CO_3$ and extracted with EtOAc. The organic layer was separated, dried, filtered and the solvent was evaporated. The residue was purified by column chromatography over silica gel (eluent: $CH_2Cl_2/CH_3OH$ 99.5/0.5). The pure fractions were collected and the solvent was evaporated. The residue was crystallized from diethyl ether. The precipitate was filtered off and dried, yielding 3.7 g (17.2%) of (±)-2,6-dichloro-α-[4-chloro-3-(trifluoromethyl)phenyl]-4-(4,5-dihydro-3,5-dioxo-1,2,4-triazin-2(3H)-yl)-α-methylbenzeneacetonitrile (comp. 1.7)

Example B.2

Boron tribromide (0.01932 mol) was added dropwise at −70° C. to a solution of inter mediate 23 (0.00322 mol) in $CH_2Cl_2$ (20 ml). The mixture was stirred at −70° C. for 5 hours, then poured out into ice water, basified with $K_2CO_3$ and extracted with $CH_2Cl_2$. The organic layer was separated, washed with $H_2O$, dried, filtered and the solvent was evaporated. The residue was purified by column chromatography over silica gel (eluent: $CH_2Cl_2/CH_3OH$ 97.5/2.5). The pure fractions were collected and the solvent was evaporated. The residue was dried, yielding 0.30 g of (±)-4-chloro-α-[2-chloro-3-(4,5-dihydro-3,5-dioxo-1,2,4-triazin-2(3H)-yl) phenyl]-α-methyl-3-(trifluoromethyl)benzeneacetonitrile (comp. 1.36).

Example B.3

2-methyl-2-propanol, potassium salt (0.0428 mol) was added in one portion at 10° C. under $N_2$ flow to a mixture of 1-[(isocyanomethyl)sulfonyl]-4-methylbenzene (0.0155 mol) in dimethyl sulfoxide (19 ml). The mixture was stirred for 10 minutes. Intermediate 29 (0.0119 mol) and methanol (0.9 ml) were added. The mixture was stirred at RT for 4 hours, then poured out into water, neutralized with HCl (3N) and extracted with EtOAc. The organic layer was separated, washed with water, dried, filtered and the solvent was evaporated. The residue was purified by column chromatography over silica gel (eluent: $CH_2Cl_2/CH_3OH$ 99/1). The pure fractions were collected and the solvent was evaporated, yielding 2.39 g (46%) of (±)-4-chloro-α-[2-chloro-3-(4,5-dihydro-3,5-dioxo-1,2,4-triazin-2(3H)-yl) phenyl]-3-(trifluoromethyl)benzeneacetonitrile (comp. 1.38).

Example B.4

A mixture of intermediate 32 (18.4 g) and copper(I) cyanide (6.7 g) was stirred for 30 minutes at 180° C. After cooling, the reaction mixture was taken up in a mixture of $CHCl_3/CH_3OH$ (90:10). The whole was filtered and the filtrate was evaporated. The residue was crystallized from a mixture of $CHCl_3/CH_3OH$ (98:2). The product was filtered off, washed with 2,2'-oxybispropane and dried, yielding 6.7 g (37.3%) of α-(4-chlorophenyl)-4-(4,5-dihydro-3,5-dioxo-1,2,4-triazin-2(3H)-yl)benzeneacetonitrile; (comp. 1.41; mp. 206.3° C.).

Example B.5

A mixture of 2-chloro-α-(4-chlorophenyl)-4-(4,5-dihydro-3,5-dioxo-1,2,4-triazin-2(3H)-yl)-α-methylbenzeneacetonitrile (0.01 mol) and triethylamine (0.01 mol) in pyridine (115 ml) was heated at 60° C. $H_2S$ was bubbled through the mixture for 5 hours. The mixture was then stirred at 60° C. for 16 hours. $H_2S$ was bubbled through the mixture again for 8 hours and the mixture was then stirred at 60° C. for 48 hours. $H_2S$ was bubbled through the mixture for 3 days. The solvent was evaporated and the residue was taken up in $CH_2Cl_2$, washed with an HCl (3N) and with water, dried, filtered and the solvent was evaporated. The residue was purified by column chromatography over silica gel (eluent: $CH_2Cl_2/CH_3OH$ 97/3). The pure fractions were collected and the solvent was evaporated, yielding 1.5 g (36%) of (±)-2-chloro-a-(4-chlorophenyl)-α-methyl-4-(4,5-dihydro-3,5-dioxo-1,2,4-triazin-2(3H)-yl) benzeneethanethioamide (comp. 1.21)

Example B.6 a) Compound 2.8 (0.00474 mol) was added portionwise to $H_2SO_4$ (5 ml), acetic acid (5 ml) and $H_2O$ (5 ml). The mixture was stirred at 140° C. for 14 hours and then poured out into $H_2O$. The precipitate was filtered off, washed with $H_2O$, taken up in EtOAc, washed with $H_2O$, dried, filtered and the solvent was evaporated. The residue was crystallized from EtOAc and diethyl ether. The precipitate was filtered off and dried, yielding 0.7 g (33%) of (±)-2,6-dichloro-α-(4-chlorophenyl)-4-(4,5-dihydro-3,5-dioxo-1,2,4-triazin-2(3H)-yl)-α-methylbenzeneacetonitrile (comp. 1.11).

b) A mixture of 2-chloro-α-(4-chlorophenyl)-4-(4,5-dihydro-3,5-dioxo-1,2,4-triazin-2(3H)-yl)-α-methylbenzeneacetonitrile (0.026 mol) in $H_2SO_4$ (75 ml), acetic acid (75 ml) and $H_2O$ (75 ml) was stirred at 140° C. for 24 hours. $H_2SO_4$ (25 ml) and acetic acid (25 ml) were added again. The mixture was stirred and refluxed for 18 hours and then poured out on ice. The precipitate was filtered off, taken up in EtOAc, washed with $H_2O$, dried, filtered and the solvent was evaporated. The residue was taken up in $CH_2Cl_2$, washed with $H_2O$, dried, filtered and the solvent was evaporated. Part of this residue (1 g) was taken up in $H_2O$ and NaOH 3N, treated with activated charcoal, filtered over celite, extracted with $CH_2Cl_2$ and separated into its layers. The aqueous layer was acidified with HCl 3N and extracted with $CH_2Cl_2$. The combined organic layer was washed with $H_2O$, dried, filtered and the solvent was evaporated, yielding 0.56 g (±)-2-chloro-α-(4-chlorophenyl)-4-(4,5-dihydro-3,5-dioxo-1,2,4-triazin-2(3H)-yl)-α-methylbenzeneacetic acid (comp. 1.12)

Example B.7 a) A mixture of 2-chloro-α-(4-chlorophenyl)-4-(4,5-dihydro-3,5-dioxo-1,2,4-triazin-2(3H)-yl)benzeneacetic acid (0.0178 mol) in thionyl chloride (30 ml) was stirred and refluxed for 2 hours. The mixture was cooled and the solvent was evaporated, yielding 6.5 g of (±)-2-chloro-α-(4-chlorophenyl)-4-(4,5-dihydro-3,5-dioxo-1,2,4-triazin-2(3H)-yl)benzeneacetyl chloride (comp. 1.5).

b) A mixture of compound 1.56 (0.0038 mol) in thionylchloride (11 ml) was stirred and refluxed for 2 hours. The solvent was evaporated, yielding (±)-2,6-dichloro-α-[4-chloro-3-(trifluoromethyl)phenyl]-4-(4,5-dihydro-3,5-dioxo-1,2,4-triazin-2(3H)-yl]-benzeneacetyl chloride (comp. 1.57).

Example B.8

A mixture of compound 1.5 (0.0158 mol), O,N-dimethylhydroxylamine (0.0237 mol) and triethylamine (0.0521 mol) in $CH_2Cl_2$ (150 ml) was stirred at RT for 12 hours. The mixture was washed with $K_2CO_3$ (10%) and with water, dried, filtered and the solvent was evaporated. The residue was taken up in $CH_2Cl_2$, washed with HCl (3N) and with water, dried, filtered and the solvent was evaporated. The residue was purified by column chromatography over silica gel (eluent: $CH_2Cl_2/CH_3OH$ 98/2). The pure fractions were collected and the solvent was evaporated. The residue was recrystallized from $CH_3CN$ and diethyl ether. The precipitate was filtered off and dried, yielding 2.15 g (34%) of (±)-2-chloro-α-(4-chlorophenyl)-N-methoxy-N-methyl-4-(4,5-dihydro-3,5-dioxo-1,2,4-triazin-2(3H)-yl) benzeneacetamide (comp. 1.6).

Example B.9

A solution of (±)-2-chloro-α-(4-chlorophenyl)-4-(4,5-dihydro-3,5-dioxo-1,2,4-triazin-2(3H)-yl)-α-methylbenzeneacetyl chloride (0.007 mol) in $CH_2Cl_2$ (20 ml) was added at RT to methanamine 40% in water (0.105 mol). The mixture was stirred at RT for 4 hours, then poured out into water, acidified with HCl (3N) and extracted with $CH_2Cl_2$. The organic layer was separated, dried, filtered and the solvent was evaporated. The residue was purified by column chromatography over silica gel (eluent: $CH_2Cl_2$/ $CH_3OH$ 97/3). The pure fractions were collected and the solvent was evaporated, yielding 1.25 g (43%) of (±)-2- chloro-α-(4-chlorophenyl)-4-(4,5-dihydro-3,5-dioxo-1,2,4-triazin-2(3H)-yl)-α,N-dimethylbenzeneacetamide (comp. 1.14).

Example B.10 n-Butyllithium, (1.6M solution in hexane; 0.0575 mol) was added at −70° C. under $N_2$ flow to a solution of benzothiazole (0.0575 mol) in THF (150 ml), and the mixture was stirred at −70° C. for 30 minutes. Compound 1.6 (0.0115 mol) in THF (100 ml) was added dropwise, the mixture was stirred at −70° C. for 3 hours, poured out into water and extracted with EtOAc. The organic layer was separated, dried, filtered, and the solvent was evaporated. The residue was purified by column chromatography over silica gel (eluent: $CH_2Cl_2/CH_3OH$ 99/1). The pure fractions were collected and the solvent was evaporated. The residue (1.7 g) was crystallized from 2-propanone. The precipitate was filtered off and dried, yielding 1.35 g of (±)-2-[4-[2-(2-benzothiazolyl)-1-(4-chlorophenyl)-2-oxoethyl]-3-chlorophenyl]-1,2,4-triazin-3,5(2H,4H)-dione (comp. 1.20).

Example B.11

Acetic acid, ammonium salt (3 g) was added at RT to a solution of (±)-2-chloro-α-(4-chlorophenyl)-4-(4,5-dihydro-3,5-dioxo-1,2,4-triazin-2(3H)-yl)-α-methylbenzeneacetyl chloride (0.007 mol) in 2-propanone (30 ml). The mixture was stirred at RT for 5 hours. Acetic acid, ammonium salt was filtered off and the solvent was evaporated. The residue was taken up in $CH_2Cl_2$, washed with water, dried, filtered and the solvent was evaporated. The residue was purified by column chromatography over silica gel (eluent: $CH_2Cl_2/CH_3OH$ 97/3). The pure fractions were collected and the solvent was evaporated, yielding 1.6 g (57%) of (±)-2-chloro-a-(4-chlorophenyl)-4-(4,5-dihydro-3,5-dioxo-1,2,4-triazin-2(3H)-yl)-α-methylbenzeneacetamide (comp. 1.18).

Example B.12

A mixture of compound 1.68 (0.031 mol) in HBr in acetic acid (110 ml; 33% solution) and HBr (65 ml; 48% aqueous solution) was stirred and refluxed overnight and then poured out into ice water. The precipitate was filtered off, washed with $H_2O$ and taken up in $CH_2Cl_2$ and a small amount of $CH_3OH$. The organic solution was dried, filtered and the solvent was evaporated, yielding 13.6 g of (±)-2,6-dichloro-α-(4-chlorophenyl)-4-(4,5-dihydro-3,5-dioxo-1,2,4-triazin-2(3H)-yl-α-methylbenzeneacetic acid; (comp. 1.69).

Example B.13

A mixture of intermediate (41) (0.00457 mol) in concentrated HCl (25 ml) and acetic acid (44 ml) was stirred and refluxed overnight. The mixture was allowed to cool to RT, poured out on ice, basified with $K_2CO_3$ and extracted with $CH_2Cl_2$ and a small amount of $CH_3OH$. The organic layer was separated, dried, filtered and the solvent was evaporated. The residue (2.1 g) was purified by column chromatography over silica gel (eluent: $CH_2Cl_2/CH_3OH/NH_4OH$ 90/10/1 and 70/30/1). The pure fractions were collected and the solvent was evaporated. The residue was crystallized from EtOAc and 2-propanone. The precipitate was filtered off and dried, yielding 0.95 g (45%) of (±)-2-chloro-α-(4-chlorophenyl)-4-(4,5-dihydro-3,5-dioxo-1,2,4-triazin-2(3H)-yl)-α-[3-(dimethylamino)propyl]-benzeneacetonitrile; mp. 140° C. (Kofler) (comp. 1.58).

Example B.14

A mixture of compound 1.5 (0.05 mol) in THF (350 ml) was stirred at −75° C. A solution of chloro(phenylmethyl) magnesium (0.1 mol; 2 M/THF) in THF (50 ml) was added dropwise over 1 hour at −75° C. The mixture was stirred at −75° C. for 4 hours, then the temperature was raised to −20° C. and a saturated $NH_4Cl$ solution (50 ml) was added dropwise over 15 minutes. Water was added and the layers were separated. The organic layer was evaporated. The residue was dissolved in $CH_2Cl_2/CH_3OH$ 90/10. The organic layer was dried, filtered and the solvent was evaporated. The residue was stirred in $CH_2Cl_2$. The solid was filtered off, the filtrate was evaporated and the residue was filtered over silica gel using a mixture of $CH_2Cl_2/CH_3OH$ 98/2 as eluent. The desired product fraction was collected and the solvent was evaporated, yielding 4.3 g (±)-2-[3-chloro-4-[1-(4-chlorophenyl)-2-oxo-3-phenylpropyl]phenyl]-1,2,4-triazine-3,5(2H,4H)-dione (comp. 1.67).

Tables 2 to 5 list the compounds of formula (I) which were prepared according to one of the above examples (column "Ex. No.")

TABLE 2

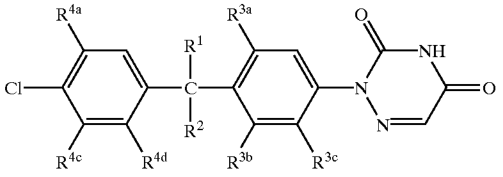

| Comp. No. | Ex. No. | $R^1$ | $R^2$ | $R^{3b}$ | $R^{3c}$ | $R^{4a}$ | $R^{4c}$ | $R^{4d}$ |
|---|---|---|---|---|---|---|---|---|
| 1.1 | B.1 | $CH_3$ | CN | H | H | Cl | H | H |
| 1.2 | B.5 | H | 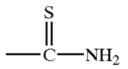 | H | H | H | H | H |
| 1.3 | B.1 | $CH_3$ | CN | H | H | $OCH_3$ | H | H |
| 1.4 | B.1 | $CH_3$ | CN | H | $CH_3$ | $CF_3$ | H | H |

TABLE 2-continued
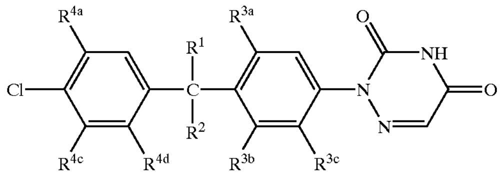
| Comp. No. | Ex. No. | $R^1$ | $R^2$ | $R^{3b}$ | $R^{3c}$ | $R^{4a}$ | $R^{4c}$ | $R^{4d}$ |
|---|---|---|---|---|---|---|---|---|
| 1.5 | B.7a | H | 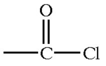 | H | H | H | H | H |
| 1.6 | B.8 | H | 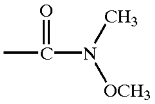 | H | H | H | H | H |
| 1.7 | B.1 | $CH_3$ | CN | Cl | H | $CF_3$ | H | H |
| 1.8 | B.8 | H | 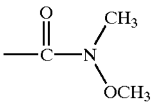 | Cl | H | H | H | H |
| 1.9 | B.1 | $CH_3$ | CN | Cl | H | Cl | H | H |
| 1.10 | B.9 | H | 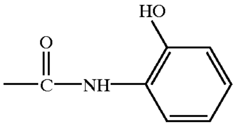 | H | H | H | H | H |
| 1.11 | B.6a | $CH_3$ | 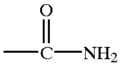 | Cl | H | H | H | H |
| 1.12 | B.6b | $CH_3$ | 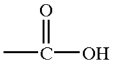 | H | H | H | H | H |
| 1.13 | B.7a | $CH_3$ | 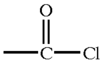 | H | H | H | H | H |
| 1.14 | B.9 | $CH_3$ | 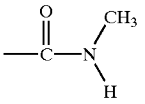 | H | H | H | H | H |
| 1.15 | B.10 | H | 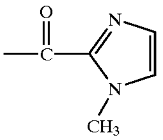 | H | H | H | H | H |
| 1.16 | B.5 | $CH_3$ | 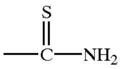 | Cl | H | H | H | H |
| 1.17 | B.1 | $CH_3$ | CN | H | H | $CH_3$ | H | H |
| 1.18 | B.11 | $CH_3$ | 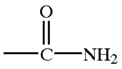 | H | H | H | H | H |
| 1.19 | B.1 | $CH_3$ | CN | H | H | H | H | Cl |

TABLE 2-continued
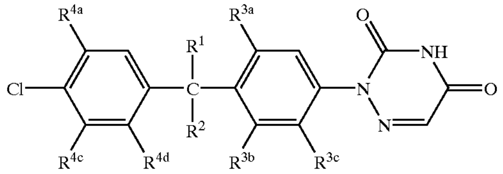
| Comp. No. | Ex. No. | $R^1$ | $R^2$ | $R^{3b}$ | $R^{3c}$ | $R^{4a}$ | $R^{4c}$ | $R^{4d}$ |
|---|---|---|---|---|---|---|---|---|
| 1.20 | B.10 | H | 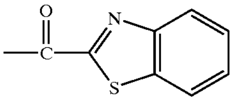 | H | H | H | H | H |
| 1.21 | B.5 | $CH_3$ | 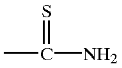 | H | H | H | H | H |
| 1.22 | B.10 | H | 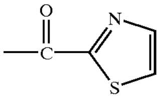 | H | H | H | H | H |
| 1.23 | B.8 | $CH_3$ | 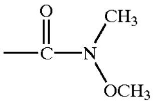 | H | H | H | H | H |
| 1.24 | B.9 | $CH_3$ | 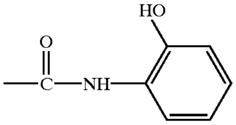 | H | H | H | H | H |
| 1.25 | B.10 | H | 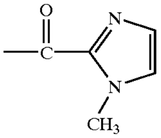 | Cl | H | H | H | H |
| 1.26 | B.5 | $CH_3$ | 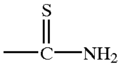 | Cl | H | $CF_3$ | H | H |
| 1.27 | B.5 | H | 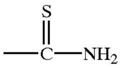 | Cl | H | $CF_3$ | H | H |
| 1.28 | B.5 | $CH_3$ | 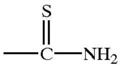 | Cl | H | Cl | H | H |
| 1.29 | B.5 | $CH_3$ | 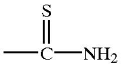 | H | $CH_3$ | $CF_3$ | H | H |
| 1.30 | B.10 | H | 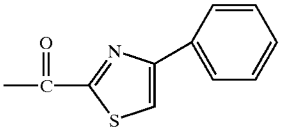 | H | H | H | H | H |
| 1.31 | B.5 | $CH_3$ | 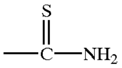 | H | H | $CF_3$ | H | H |

TABLE 2-continued
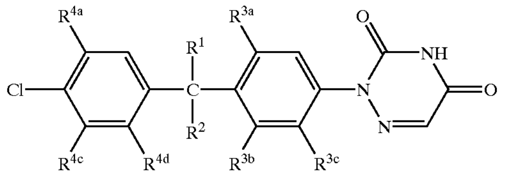
| Comp. No. | Ex. No. | $R^1$ | $R^2$ | $R^{3b}$ | $R^{3c}$ | $R^{4a}$ | $R^{4c}$ | $R^{4d}$ |
|---|---|---|---|---|---|---|---|---|
| 1.32 | B.6b | $CH_3$ | 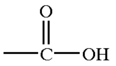 | H | H | $CF_3$ | H | H |
| 1.33 | B.7a | $CH_3$ | 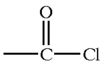 | H | H | $CF_3$ | H | H |
| 1.34 | B.6b | 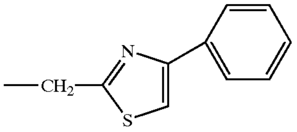 | 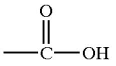 | H | H | H | H | H |
| 1.53 | B.1 | $CH_3$ | CN | Cl | H | $CF_3$ | H | H |
| 1.54 | B.1 | $CH_3$ | CN | Cl | H | $CF_3$ | H | H |
| 1.55 | B.5 | $CH_3$ | 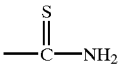 | H | H | $CH_3$ | H | H |
| 1.56 | B.6b | H | 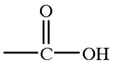 | Cl | H | $CF_3$ | H | H |
| 1.57 | B.7b | H | 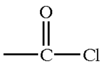 | Cl | H | $CF_3$ | H | H |
| 1.58 | B.13 | $(CH_2)_3—N(CH_3)_2$ | CN | H | H | H | H | H |
| 1.59 | B.1 | H | CN | Cl | H | $CH_3$ | H | H |
| 1.60 | B.5 | H | 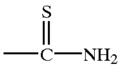 | Cl | H | $CH_3$ | H | H |
| 1.61 | B.14 | H | 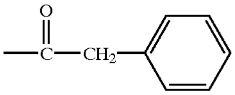 | Cl | H | H | H | H |
| 1.62 | B.14 | H | 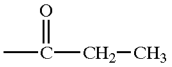 | Cl | H | H | H | H |
| 1.63 | B.1 | $CH_3$ | CN | Cl | H | F | H | H |
| 1.64 | B.5 | $CH_3$ | 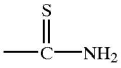 | Cl | H | F | H | H |
| 1.65 | B.1 | H | CN | Cl | H | $CH_3O$ | H | H |
| 1.66 | B.5 | H | 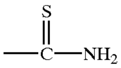 | Cl | H | $CH_3O$ | H | H |
| 1.67 | B.14 | H | 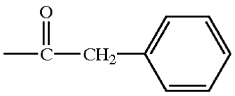 | H | H | H | H | H |

TABLE 2-continued

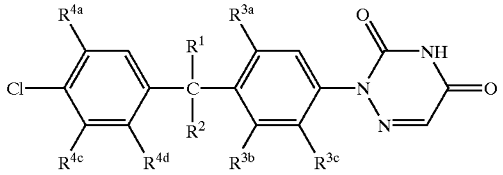

| Comp. No. | Ex. No. | $R^1$ | $R^2$ | $R^{3b}$ | $R^{3c}$ | $R^{4a}$ | $R^{4c}$ | $R^{4d}$ |
|---|---|---|---|---|---|---|---|---|
| 1.68 | B.1 | $CH_3$ | 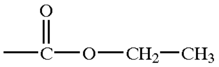 | Cl | H | H | H | H |
| 1.69 | B.12 | $CH_3$ | 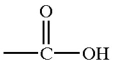 | Cl | H | H | H | H |
| 1.70 | B.7a | $CH_3$ | 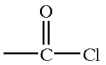 | Cl | H | H | H | H |

TABLE 3

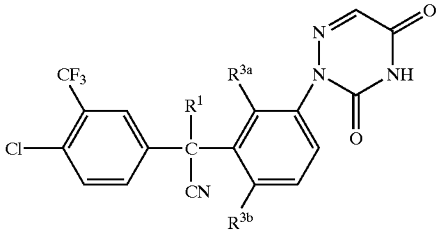

| Comp. No. | Ex. No. | $R^1$ | $R^{3a}$ | $R^{3b}$ |
|---|---|---|---|---|
| 1.35 | B.2 | $CH_3$ | H | Cl |
| 1.36 | B.2 | $CH_3$ | Cl | H |

TABLE 3-continued

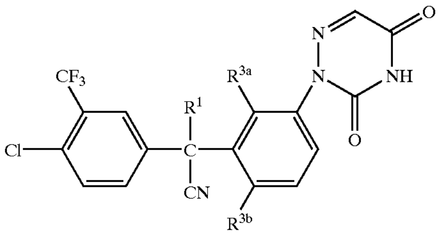

| Comp. No. | Ex. No. | $R^1$ | $R^{3a}$ | $R^{3b}$ |
|---|---|---|---|---|
| 1.37 | B.3 | H | H | Cl |
| 1.38 | B.3 | H | Cl | H |

TABLE 4

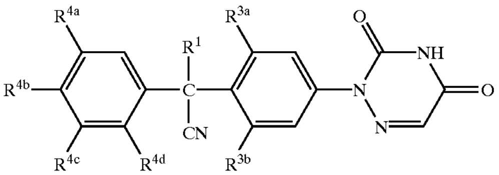

| Comp. No. | Ex. No. | $R^1$ | $R^{3a}$ | $R^{3b}$ | $R^{4a}$ | $R^{4b}$ | $R^{4c}$ | $R^{4d}$ |
|---|---|---|---|---|---|---|---|---|
| 1.39 | B.1 | H | Cl | Cl | H | H | H | H |
| 1.40 | B.1 | H | Cl | Cl | H | $OCH_3$ | H | H |
| 1.41 | B.4 | H | H | H | H | Cl | H | H |
| 1.42 | B.1 | $CH_3$ | Cl | H | $OCH_3$ | $OCH_3$ | H | H |
| 1.43 | B.1 | $CH_3$ | Cl | H | H | $OCH_3$ | H | H |
| 1.44 | B.1 | $CH_3$ | Cl | H | Cl | $OCH_3$ | H | H |
| 1.45 | B.1 | $CH_3$ | $OCH_3$ | H | $CF_3$ | Cl | H | H |
| 1.46 | B.1 | $CH_3$ | Cl | H | $OCH_3$ | $OCH_3$ | $OCH_3$ | H |
| 1.47 | B.1 | $CH_3$ | Cl | H | $CH_3$ | $OCH_3$ | H | H |
| 1.48 | B.1 | $CH_3$ | H | H | H | Cl | H | Cl |
| 1.49 | B.1 | $CH_3$ | $CH_3$ | H | $CF_3$ | Cl | H | H |
| 1.50 | B.1 | $CH_3$ | Cl | H | H | phenyl | H | H |

TABLE 4-continued

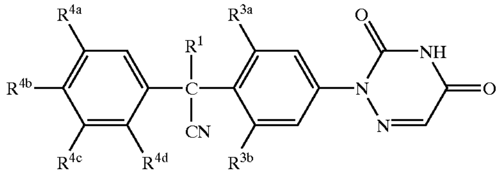

| Comp. No. | Ex. No. | $R^1$ | $R^{3a}$ | $R^{3b}$ | $R^{4a}$ | $R^{4b}$ | $R^{4c}$ | $R^{4d}$ |
|---|---|---|---|---|---|---|---|---|
| 1.51 | B.1 | H | Cl | Cl | $CF_3$ | Cl | H | H |
| 1.52 | B.2 | 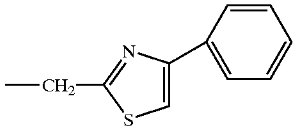 | Cl | H | H | Cl | H | H |
| 1.71 | B.1 | H | $CH_3$ | $CH_3$ | Cl | Cl | H | H |
| 1.72 | B.1 | H | Br | Br | H | Cl | H | H |

TABLE 5

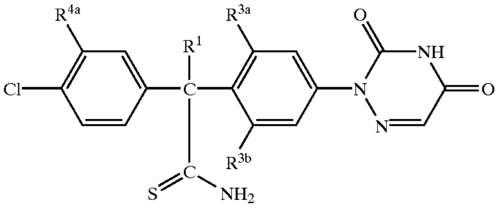

| Comp. No. | Ex. No. | $R^1$ | $R^{3a}$ | $R^{3b}$ | $R^{4a}$ |
|---|---|---|---|---|---|
| 1.73 | B.5 | $CH_3$ | $CH_3O$ | H | $CF_3$ |
| 1.74 | B.5 | H | $CH_3$ | $CH_3$ | Cl |
| 1.75 | B.5 | H | Br | Br | H |

Table 6 lists both the experimental (column heading "Exp") and theoretical (column heading "Theor") elemental analysis values for carbon (C), hydrogen (H) and nitrogen (N) for the compounds as prepared in the experimental part hereinabove.

TABLE 6

| Comp. | C | | H | | N | |
|---|---|---|---|---|---|---|
| No. | Theor | Exp | Theor | Exp | Theor | Exp |
| 1.1 | 51.27 | 51.28 | 2.63 | 2.21 | 13.29 | 13.06 |
| 1.2 | 50.13 | 49.72 | 2.97 | 2.62 | 13.76 | 12.95 |
| 1.3 | 54.69 | 54.04 | 3.38 | 3.44 | 13.43 | 12.96 |
| 1.4 | 51.19 | 51.3 | 2.79 | 2.71 | 11.94 | 11.75 |
| 1.6 | 52.43 | 52.25 | 3.71 | 3.89 | 12.87 | 12.69 |
| 1.7 | 46.60 | 46.8 | 2.06 | 2.00 | 11.44 | 11.3 |
| 1.8 | 48.59 | 48.22 | 3.22 | 2.90 | 11.93 | 11.45 |
| 1.9 | 47.40 | 47.25 | 2.21 | 2.22 | 12.28 | 11.95 |
| 1.11 | 49.17 | 49.47 | 2.98 | 3.11 | 12.74 | 11.92 |
| 1.12 | 53.22 | 51.73 | 3.23 | 3.17 | 10.34 | 9.88 |
| 1.14 | 54.43 | 53.2 | 3.85 | 3.88 | 13.36 | 12.85 |
| 1.15 | 55.28 | 54.18 | 3.31 | 3.39 | 15.35 | 14.83 |
| 1.17 | 56.87 | 56.33 | 3.52 | 3.46 | 13.96 | 13.43 |
| 1.18 | 53.35 | 51.78 | 3.48 | 3.53 | 13.83 | 13.17 |
| 1.19 | 51.27 | 51.38 | 2.63 | 2.67 | 13.29 | 13.15 |
| 1.20 | 56.59 | 56.45 | 2.77 | 2.66 | 11 | 10.77 |

TABLE 6-continued

| Comp. | C | | H | | N | |
|---|---|---|---|---|---|---|
| No. | Theor | Exp | Theor | Exp | Theor | Exp |
| 1.21 | 51.32 | 49.63 | 3.35 | 3.35 | 13.3 | 12.62 |
| 1.22 | 52.3 | 54.18 | 2.63 | 2.9 | 12.2 | 11.54 |
| 1.23 | 53.47 | 52.5 | 4.04 | 3.93 | 12.47 | 12.14 |
| 1.25 | 51.4 | 51.48 | 2.88 | 2.98 | 14.27 | 13.91 |
| 1.30 | 58.33 | 58.25 | 3.01 | 3.04 | 10.46 | 10.27 |
| 1.35 | 50.13 | 50.21 | 2.44 | 2.35 | 12.31 | 12.12 |
| 1.36 | 50.13 | 50.19 | 2.44 | 2.51 | 12.31 | 11.79 |
| 1.37 | 49 | 49.34 | 2.06 | 1.88 | 12.7 | 12.45 |
| 1.42 | 58.19 | 58.31 | 4.15 | 4.23 | 13.57 | 13.44 |
| 1.43 | 59.61 | 57.79 | 3.95 | 3.87 | 14.64 | 14.19 |
| 1.44 | 54.69 | 54.78 | 3.38 | 3.46 | 13.43 | 13.06 |
| 1.45 | 53.29 | 53.3 | 3.13 | 3.08 | 12.43 | 12.14 |
| 1.46 | 56.96 | 56.13 | 4.32 | 4.13 | 12.65 | 12.4 |
| 1.47 | 60.53 | 60.78 | 4.32 | 4.41 | 14.12 | 13.63 |
| 1.48 | 55.83 | 55.83 | 3.12 | 3.08 | 14.47 | 14.30 |
| 1.49 | 55.25 | 55.36 | 3.25 | 3.21 | 12.89 | 12.90 |
| 1.50 | 67.21 | 65.87 | 4.00 | 4.13 | 13.06 | 12.68 |
| 1.52 | 59.35 | 59.39 | 3.14 | 3.04 | 12.82 | 12.63 |
| 1.53 | 46.60 | 46.62 | 2.06 | 1.95 | 11.44 | 11.37 |
| 1.54 | 46.60 | 46.51 | 2.06 | 1.96 | 11.44 | 11.44 |
| 1.58 | 57.65 | 56.55 | 4.62 | 4.65 | 15.28 | 14.12 |
| 1.61 | 57.56 | 57.62 | 3.22 | 3.22 | 8.39 | 8.45 |
| 1.71 | 56.87 | 56.69 | 3.52 | 3.58 | 13.96 | 13.41 |

C. Pharmacological Example

Example C.1

In Vitro Inhibition of IL-5 Production In Human Blood

Human Whole Blood Stimulation

Peripheral blood from healthy male donors was drawn into heparinized syringes (12.5 U heparin/ml). Blood samples were three-fold diluted in RMPI 1640 medium (Life Technologies, Belgium) supplemented with 2 mM L-glutamine, 100 U/ml penicillin and 100 $\mu$g/ml streptomycin, and 300 $\mu$l fractions were distributed in 24-well multidisc plates. Blood samples were preincubated (60 minutes at 37° C.) in a humidified 6% $CO_2$-atmosphere with 100 $\mu$l of drug solvent (final concentration 0.02% dimethylsulfoxide in RPMI 1640) or with 100 $\mu$l of an appropriate dose of test compound before being stimulated by the addition of 100 μl of phytohemagglutinin HA17 (Murex, UK) at a final concentration of 2 μg/ml. After 48 hours, cell-free supernatant fluids were collected by centrifugation and stored at −70° C. until tested for the presence of IL-5.

IL-5 Measurements

IL-5 measurements were conducted as described in Van Wauwe et al. (1996, Inflamm Res, 45, 357–363) on page 358 using ELISA.

Table 8 lists the percentage inhibition of IL-5 production (column "% inhibition") at a test dose of $1\times10^{-6}$ M, or in case the percentage inhibition is marked with an "*" $1\times10^{-5}$ M, for the compounds of the present invention including compounds of formula (I) which have been disclosed in U.S. Pat. No. 4,631,278 (Ref. A) or U.S. Pat. No. 4,767,760 (Ref. B) as summarized in table 7.

TABLE 7

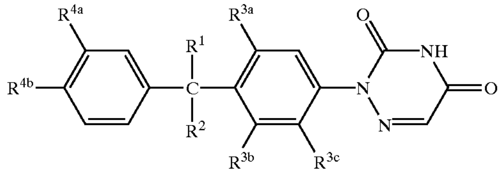

| Co. No. | Ref | $R^1$ | $R^2$ | $R^{3a}$ | $R^{3b}$ | $R^{3c}$ | $R^{4a}$ | $R^{4b}$ |
|---|---|---|---|---|---|---|---|---|
| 2.1 | A | $CH_3$ | CN | H | H | H | H | H |
| 2.2 | A | $CH_3$ | CN | Cl | H | H | H | F |
| 2.3 | A | $CH_3$ | CN | $CF_3$ | H | H | H | Cl |
| 2.4 | A | 4-chlorophenyl | CN | Cl | H | H | H | Cl |
| 2.5 | A | $(CH_2)_2$—$CH_3$ | CN | Cl | H | H | H | Cl |
| 2.6 | A | $(CH_2)_3$—$CH_3$ | CN | Cl | H | H | H | Cl |
| 2.7 | A | $CH_3$ | CN | Cl | H | H | $CF_3$ | Cl |
| 2.8 | A | $CH_3$ | CN | Cl | Cl | H | H | Cl |
| 2.9 | A | H | CN | Cl | H | H | H | Cl |
| 2.10 | A | $CH_3$ | CN | Cl | $CH_3$ | H | H | Cl |
| 2.11 | A | $CH_3$ | CN | Cl | H | $CH_3$ | H | Cl |
| 2.12 | A | H | CN | Cl | Cl | H | H | Cl |
| 2.13 | A | H | CN | Cl | H | H | H | F |
| 2.14 | A | H | CN | Cl | H | H | H | $CH_3$ |
| 2.15 | A | $CH_3$ | CN | F | H | H | H | F |
| 2.16 | A | H | CN | Cl | Cl | H | H | F |
| 2.17 | A | H | CN | Cl | $CH_3$ | H | H | F |
| 2.18 | A | H | CN | $CH_3$ | $CH_3$ | H | H | F |
| 2.19 | A | H | CN | $CH_3$ | $CH_3$ | H | H | Cl |
| 2.20 | B | H | C(=O)NHCH$_3$ | Cl | Cl | H | H | Cl |
| 2.21 | B | H | 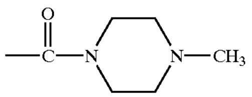 | Cl | Cl | H | H | Cl |
| 2.22 | B | H | C(=O)CH$_3$ | Cl | Cl | H | H | Cl |
| 2.23 | B | H | C(=S)NH$_2$ | Cl | Cl | H | H | Cl |

TABLE 8

| Co. No. | % inhibition |
|---|---|
| 1.1 | 63 |
| 1.2 | 11 |
| 1.3 | 40 |
| 1.4 | 87 |
| 1.6 | 49 |
| 1.7 | 92 |
| 1.8 | 42 |

TABLE 8-continued

| Co. No. | % inhibition |
|---|---|
| 1.9 | 84 |
| 1.11 | 12 |
| 1.14 | 9 |
| 1.15 | 70 |
| 1.17 | 63 |
| 1.19 | 49 |
| 1.20 | 80 |
| 1.21 | 33 |
| 1.23 | 62 |
| 1.24 | 12 |
| 1.25 | 6 |
| 1.35 | 33 |
| 1.36 | 44 |
| 1.37 | 12 |
| 1.39 | 31 |

TABLE 8-continued

| Co. No. | % inhibition |
|---|---|
| 1.41 | 13 |
| 1.42 | 22 |
| 1.43 | 5 |
| 1.44 | 46 |
| 1.45 | 41 |
| 1.46 | 33 |
| 1.47 | 38 |

TABLE 8-continued

| Co. No. | % inhibition |
|---|---|
| 1.48 | 2 |
| 1.49 | 69 |
| 1.50 | 24 |
| 1.53 | 95 |
| 1.54 | 95 |
| 1.58 | 28 |
| 1.61 | 72 |
| 1.71 | 23 |
| 2.1 | 14 |
| 2.2 | 22 |
| 2.3 | 37 |
| 2.4 | 16 |
| 2.5 | 67 |
| 2.6 | 81 |
| 2.7 | 85 |
| 2.8 | 87 |
| 2.9 | 21 |
| 2.10 | 81 |
| 2.11 | 53 |
| 2.12 | 37 |
| 2.13 | 48* |
| 2.14 | 37 |
| 2.15 | 14 |
| 2.16 | 10 |
| 2.17 | 23 |
| 2.18 | 9 |
| 2.19 | 20 |
| 2.20 | 31 |
| 2.21 | 25 |
| 2.22 | 83 |
| 2.23 | 47 |

D. Composition Examples

The following formulations exemplify typical pharmaceutical compositions suitable for systemic or topical administration to animal and human subjects in accordance with the present invention.

"Active ingredient" (A.I.) as used throughout these examples relates to a compound of formula (I) or a pharmaceutically acceptable addition salt thereof.

Example D.1

Film-Coated Tablets

Preparation of Tablet Core

A mixture of A.I. (100 g), lactose (570 g) and starch (200 g) was mixed well and thereafter humidified with a solution of sodium dodecyl sulfate (5 g) and polyvinyl-pyrrolidone (10 g) in about 200 ml of water. The wet powder mixture was sieved, dried and sieved again. Then there was added microcrystalline cellulose (100 g) and hydrogenated vegetable oil (15 g). The whole was mixed well and compressed into tablets, giving 10.000 tablets, each comprising 10 mg of the active ingredient.

Coating

To a solution of methyl cellulose (10 g) in denaturated ethanol (75 ml) there was added a solution of ethyl cellulose (5 g) in dichloromethane (150 ml). Then there were added dichloromethane (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinyl-pyrrolidone (5 g) and concentrated color suspension (30 ml) and the whole was homogenated. The tablet cores were coated with the thus obtained mixture in a coating apparatus.

Example D.2

2% Topical Cream

To a solution of hydroxypropyl β-cyclodextrine (200 mg) in purified water is added A.I. (20 mg) while stirring. Hydrochloric acid is added until complete dissolution and next sodium hydroxide is added until pH 6.0. While stirring, glycerol (50 mg) and polysorbate 60 (35 mg) are added and the mixture is heated to 70° C. The resulting mixture is added to a mixture of mineral oil (100 mg), stearyl alcohol (20 mg), cetyl alcohol (20 mg), glycerol monostearate (20 mg) and sorbate 60 (15 mg) having a temperature of 70° C. while mixing slowly. After cooling down to below 25° C., the rest of the purified water q.s. ad 1 g is added and the mixture is mixed to homogenous.

What is claimed is:

1. A method for treating an eosinophil-dependent inflammatory disease in a warm-blooded animal in need thereof comprising administering to the warm-blooded animal an effective amount of a compound of formula (I)

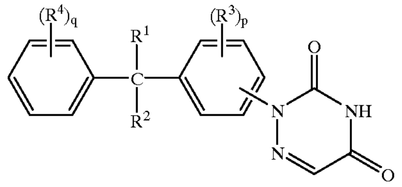

a N-oxide, a pharmaceutically acceptable addition salt or a stereochemically isomeric form thereof, wherein:

p represents 0, 1, or 2;

q represents 0, 1, 2, or 3;

$R^1$ hydrogen, $C_{1-6}$alkyl, aryl, mono-or di($C_{1-6}$alkyl) amino$C_{1-6}$alkyl, or Het $C_{1-6}$alkyl;

$R^2$ represents cyano or a radical of formula —C(=X)—Y—$R^5$; wherein

X represents O or S;

Y represents O, S, $NR^6$ or a direct bond;

$R^5$ represents hydrogen; $C_{1-6}$alkyl or aryl; and where Y is a direct bond, $R^5$ may also be halo, Het or $C_{1-6}$alkyl substituted with aryl;

$R^6$ represents hydrogen or $C_{1-6}$alkyloxy;

each $R^3$ independently represents halo, halo$C_{1-6}$ alkyl, $C_{1-6}$alkyl, $C_{1-6}$alkyloxy, $C_{1-6}$alkylthio, or aryl;

each $R^4$ independently represents halo, halo$C_{1-6}$ alkyl, $C_{1-6}$alkyl, $C_{1-6}$alkyloxy, $C_{1-6}$alkylthio, or aryl;

aryl represents phenyl or phenyl substituted with one, two or three substituents selected from the group comprising halo, hydroxy, mercapto, and $C_{1-6}$alkyl; and Het represents optionally substituted imidazolyl, thiazolyl, piperazinyl, or benzothiazolyl.

2. The method according to claim 1 wherein the eosinophil-dependent inflammatory disease is bronchial asthma.

3. The method according to claim 1 wherein the eosinophil-dependent inflammatory disease is atopic dermatitis.

4. The method according to claim 1 wherein the eosinophil-dependent inflammatory disease is allergic rhinitis.

5. The method according to claim 1 wherein the eosinophil-dependent inflammatory disease is allergic conjunctivitis.

6. The method according to claim 1 wherein the 6-azauracil moiety is in the para position relative to the central chiral carbon atom; p is 1 or 2 and one $R^3$ substituent is chloro positioned ortho relative to the central chiral carbon atom; q is 1 or 2 and one $R^4$ substituent is chloro in the 4 position.

7. A compound of formula (I')

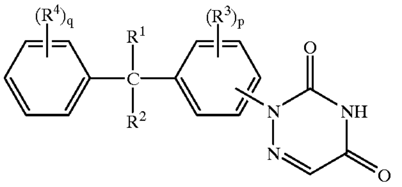

a N-oxide, a pharmaceutically acceptable addition salt or a stereochemically isomeric form thereof, wherein p, q, $R^1$, $R^3$ and $R^4$ are as defined in claim 1, and; $R^2$ represents a radical of formula —C(=X)—Y—$R^5$; wherein Y is a direct bond and $R^5$ is Het as defined in claim 1.

8. A compound as claimed in claim 7 wherein the 6-azauracil moiety is in the para position relative to the central chiral carbon atom; p is 1 or 2 and one $R^3$ substituent is chloro positioned ortho relative to the central chiral carbon atom; q is 1 or 2 and one $R^4$ substituent is chloro in the 4 position.

9. A compound as claimed in claim 7 wherein $R^1$ is mono- or di($C_{1-6}$alkyl)amino $C_{1-6}$alkyloxy, mercapto, $C_{1-6}$alkylthio or $C_{1-6}$alkyl substituted with mono- or di($C_{1-6}$alkyl)amino, $C_{1-6}$alkyloxy or Het.

10. A process for preparing a compound of formula (I') as claimed in claim 7, comprising, a) cyclizing an intermediate of formula (II) and eliminating an electron attracting group E from the thus obtained dione of formula (III):

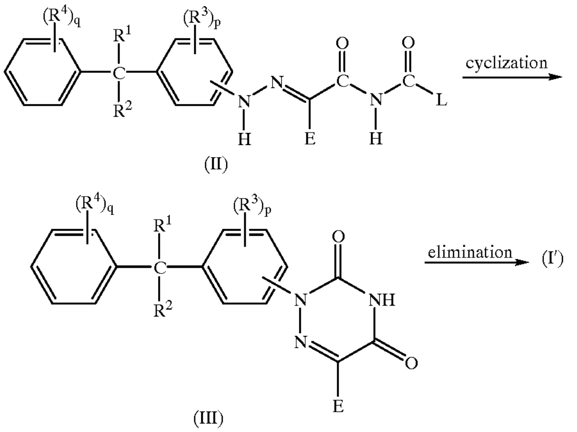

(II)

(III)

b) eliminating a protective group P in the intermediates of formula (IV):

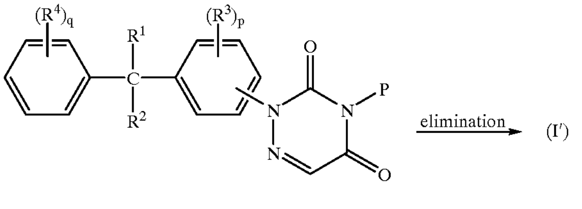

(IV)

c) converting a hydroxyl function of an intermediate of formula (V) into a suitable leaving group W, and subsequently converting said leaving group W in the thus formed intermediate of formula (VI) into a nitrile function; thus forming a compound of formula (I'-a):

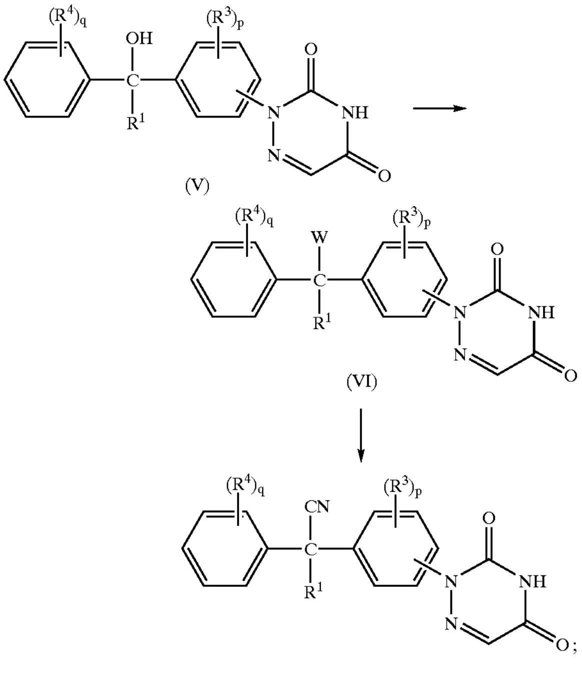

(V)

(VI)

(I'-a)

d) reacting a carbonyl group in an intermediate of formula (VII) with 1-[(isocyanomethyl)sulfonyl]-4-methylbenzene or a functional derivative thereof:

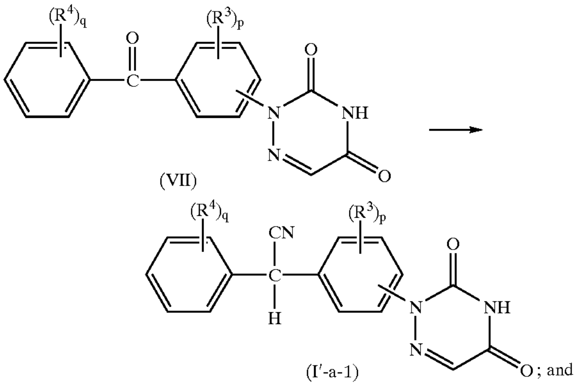

(VII)

(I'-a-1)

; and e) converting compounds of formula (I') into each other following art-known transformations, and optionally converting the compounds of formula (I'), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; and optionally preparing stereochemically isomeric forms or N-oxide forms thereof.

11. A composition comprising a pharmaceutically acceptable carrier and, as active ingredient, a therapeutically effective amount of a compound as claimed in claim 7.

12. The method of claim 1, wherein said optionally substituted imidazolyl, thiazolyl, piperazinyl, or benzothiazolyl, comprises an imidazolyl, thiazolyl, piperazinyl, or benzothiazolyl substituted with one, two or three substituents selected from aryl and $C_{1-4}$alkyl.

13. A compound of Formula (1):

(I)

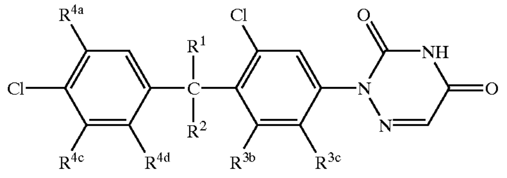

wherein said compound is selected from the group consisting of:

a compound wherein $R^1$ is H, wherein $R^2$ is

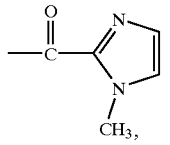

wherein $R^{3b}$ is H, wherein $R^{3c}$ is H, wherein $R^{4a}$ is H, wherein $R^{4c}$ is H, and wherein $R^{4d}$ is H;

a compound wherein $R^1$ is H, wherein $R^2$ is

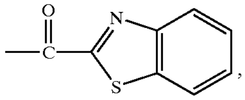

wherein $R^{3b}$ is H, wherein $R^{3c}$ is H, wherein $R^{4a}$ is H, wherein $R^{4c}$ is H, and wherein $R^{4d}$ is H;

a compound wherein $R^1$ is H, wherein $R^2$ is

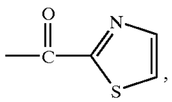

wherein $R^{3b}$ is H, wherein $R^{3c}$ is H, wherein $R^{4a}$ is H, wherein $R^{4c}$ is H, and wherein $R^{4d}$ is H;

a compound wherein $R^1$ is H, wherein $R^2$ is

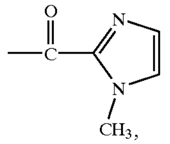

wherein $R^{3b}$ is Cl, wherein $R^{3c}$ is H, wherein $R^{4a}$ is H, wherein $R^{4c}$ is H, and wherein $R^{4d}$ is H;

a compound wherein $R^1$ is H, wherein $R^2$ is

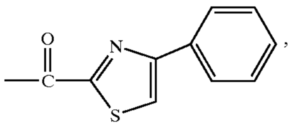

wherein $R^{3b}$ is H, wherein $R^{3c}$ is H, wherein $R^{4a}$ is H, wherein $R^{4c}$ is H, and wherein $R^{4d}$ is H; and enantiomers, diastereomers, tautomers, solvates, and pharmaceutically acceptable salts thereof.

14. A method for treating an eosinophil-dependent inflammatory disease in a warm-blooded animal in need thereof comprising administering to the warm-blooded animal an effective amount of a compound of Formula (1):

(I)

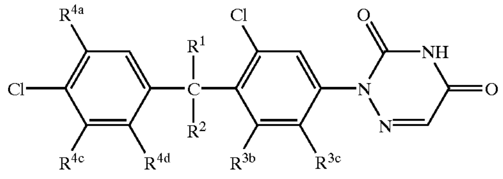

wherein said compound is selected from the group consisting of:

a compound wherein $R^1$ is $CH_3$, wherein $R^2$ is CN, wherein $R^{3b}$ H, where in $R^{3c}$ is H, wherein $R^{4a}$ is Cl, wherein $R^{4c}$ is H, and wherein $R^{4d}$ is H;

a compound wherein $R^1$ is H, wherein $R^2$ is

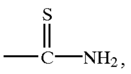

wherein $R^{3b}$ is H, wherein $R^{3c}$ is H, wherein $R^{4a}$ is H, wherein $R^{4c}$ is H, and wherein $R^{4d}$ is H;

a compound wherein $R^1$ is $CH_3$, wherein $R^2$ is CN, wherein $R^{3b}$ is H, wherein $R^{3c}$ is H, wherein $R^{4a}$ is $OCH_3$, wherein $R^{4c}$ is H, and wherein $R^{4d}$ is H;

a compound wherein $R^1$ is $CH_3$, wherein $R^2$ CN, wherein $R^{3b}$ is H, where in $R^{3c}$ is $CH_3$, wherein $R^{4a}$ is $CF_3$, wherein $R^{4c}$ is H, and wherein $R^{4d}$ is H;

a compound wherein $R^1$ is H, wherein $R^2$ is

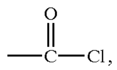

wherein $R^{3b}$ is H, wherein $R^{3c}$ is H, wherein $R^{4a}$ is H, wherein $R^{4c}$ is H, and wherein $R^{4d}$ is H;

a compound wherein $R^1$ is H, wherein $R^2$ is

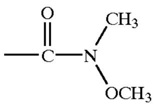

wherein $R^{3b}$ is H, wherein $R^{3c}$ is H, wherein $R^{4a}$ is H, wherein $R^{4c}$ is H, and wherein $R^{4d}$ is H;

a compound wherein $R^1$ is $CH_3$, wherein $R^2$ is CN, wherein $R^{3b}$ is Cl, where in $R^{3c}$ is H, wherein $R^{4a}$ is $CF_3$, wherein $R^{4c}$ is H, and wherein $R^{4d}$ is H;

a compound wherein $R^1$ is H, wherein $R^2$ is

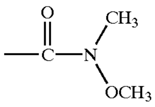

wherein $R^{3b}$ is Cl, wherein $R^{3c}$ is H, wherein $R^{4a}$ is H, wherein $R^{4c}$ is H, and wherein $R^{4d}$ is H;

a compound wherein $R^1$ is $CH_3$, wherein $R^2$ is CN, wherein $R^{3b}$ is Cl, wherein $R^{3c}$ is H, wherein $R^{4a}$ is Cl, wherein $R^{4c}$ is H, and wherein $R^{4d}$ is H;

a compound wherein $R^1$ is H, wherein $R^2$ is

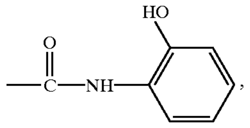

wherein $R^{3b}$ is H, wherein $R^{3c}$ is H, wherein $R^{4a}$ is H, wherein $R^{4c}$ is H, and wherein $R^{4d}$ is H;

a compound wherein $R^1$ is $CH_3$, wherein $R^2$ is

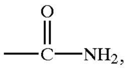

wherein $R^{3b}$ is Cl, wherein $R^{3c}$ is H, wherein $R^{4a}$ is H, wherein $R^{4c}$ is H, and wherein $R^{4d}$ is H;

a compound wherein $R^1$ is $CH_3$, wherein $R^2$ is

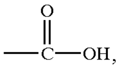

wherein $R^{3b}$ is H, wherein $R^{3c}$ is H, wherein $R^{4a}$ is H, wherein $R^{4c}$ is H, and wherein $R^{4d}$ is H;

a compound wherein $R^1$ is $CH_3$, wherein $R^2$ is

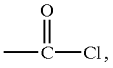

wherein $R^{3b}$ is H, wherein $R^{3c}$ is H, wherein $R^{4a}$ is H, wherein $R^{4c}$ is H, and wherein $R^{4d}$ is H;

a compound wherein $R^1$ is $CH_3$, wherein $R^2$ is

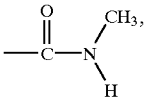

wherein $R^{3b}$ is H, wherein $R^{3c}$ is H, wherein $R^{4a}$ is H, wherein $R^{4c}$ is H, and wherein $R^{4d}$ is H;

a compound wherein $R^1$ is H, wherein $R^2$ is

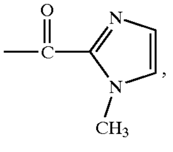

wherein $R^{3b}$ is H, wherein $R^{3c}$ is H, wherein $R^{4a}$ is H, wherein $R^{4c}$ is H, and wherein $R^{4d}$ is H;

a compound wherein $R^1$ is $CH_3$, wherein $R^2$ is

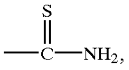

wherein $R^{3b}$ is Cl, wherein $R^{3c}$ is H, wherein $R^{4a}$ is H, wherein $R^{4c}$ is H, and wherein $R^{4d}$ is H;

a compound wherein $R^1$ is $CH_3$, wherein $R^2$ is CN, wherein $R^{3b}$ is H, wherein $R^{3c}$ is H, wherein $R^{4a}$ is $CH_3$, wherein $R^{4c}$ is H, and wherein $R^{4d}$ is H;

a compound wherein $R^1$ is $CH_3$, wherein $R^2$ is

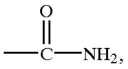

wherein $R^{3b}$ is H, wherein $R^{3c}$ is H, wherein $R^{4a}$ is H, wherein $R^{4c}$ is H, and wherein $R^{4d}$ is H;

a compound wherein $R^1$ is $CH_3$, wherein $R^2$ is CN, wherein $R^{3b}$ is H, where in $R^{3c}$ is H, wherein $R^{4a}$ is H, wherein $R^{4c}$ is H, and wherein $R^{4d}$ is Cl;

a compound wherein $R^1$ is H, wherein $R^2$ is

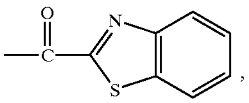

wherein $R^{3b}$ is H, wherein $R^{3c}$ is H, wherein $R^{4a}$ is H, wherein $R^{4c}$ is H, and wherein $R^{4d}$ is H;

a compound wherein $R^1$ is $CH_3$, wherein $R^2$ is

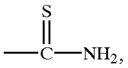

wherein $R^{3b}$ is H, wherein $R^{3c}$ is H, wherein $R^{4a}$ is H, wherein $R^{4c}$ is H, and wherein $R^{4d}$ is H;

a compound wherein $R^1$ is H, wherein $R^2$ is

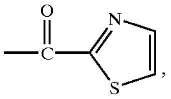

wherein $R^{3b}$ is H, wherein $R^{3c}$ is H, wherein $R^{4a}$ is H, wherein $R^{4c}$ is H, and wherein $R^{4d}$ is H;

a compound wherein $R^1$ is $CH_3$, wherein $R^2$ is

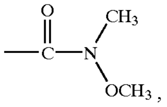

wherein $R^{3b}$ is H, wherein $R^{3c}$ is H, wherein $R^{4a}$ is H, wherein $R^{4c}$ is H, and wherein $R^{4d}$ is H;

a compound wherein $R^1$ is $CH_3$, wherein $R^2$ is

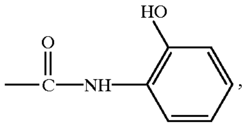

wherein $R^{3b}$ is H, wherein $R^{3c}$ is H, wherein $R^{4a}$ is H, wherein $R^{4c}$ is H, and wherein $R^{4d}$ is H;

a compound wherein $R^1$ is H, wherein $R^2$ is

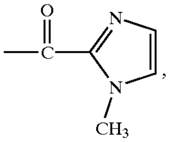

wherein $R^{3b}$ is Cl, wherein $R^{3c}$ is H, wherein $R^{4a}$ is H, wherein $R^{4c}$ is H, and wherein $R^{4d}$ is H;

a compound wherein $R^1$ is $CH_3$, wherein $R^2$ is

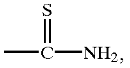

wherein $R^{3b}$ is Cl, wherein $R^{3c}$ is H, wherein $R^{4a}$ is $CF_3$, wherein $R^{4c}$ is H, and wherein $R^{4d}$ is H;

a compound wherein $R^1$ is H, wherein $R^2$ is

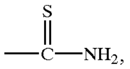

wherein $R^{3b}$ is Cl, wherein $R^{3c}$ is H, wherein $R^{4a}$ is $CF_3$, wherein $R^{4c}$ is H, and wherein $R^{4d}$ is H;

a compound wherein $R^1$ is $CH_3$, wherein $R^2$ is

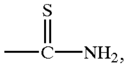

wherein $R^{3b}$ is Cl, wherein $R^{3c}$ is H, wherein $R^{4a}$ is Cl, wherein $R^{4c}$ is H, and wherein $R^{4d}$ is H;

a compound wherein $R^1$ is $CH_3$, wherein $R^2$ is

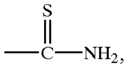

wherein $R^{3b}$ is H, wherein $R^{3c}$ is $CH_3$, wherein $R^{4a}$ is $CF_3$, wherein $R^{4c}$ is H, and wherein $R^{4d}$ is H;

a compound wherein $R^1$ is H, wherein $R^2$ is

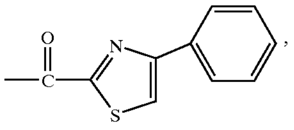

wherein $R^{3b}$ is H, wherein $R^{3c}$ is H, wherein $R^{4a}$ is H, wherein $R^{4c}$ is H, and wherein $R^{4d}$ is H;

a compound wherein $R^1$ is $CH_3$, wherein $R^2$ is

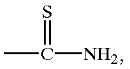

wherein $R^{3b}$ is H, wherein $R^{3c}$ is H, wherein $R^{4a}$ is $CF_3$, wherein $R^{4c}$ is H, and wherein $R^{4d}$ is H;

a compound wherein $R^1$ is $CH_3$, wherein $R^2$ is

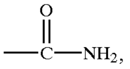

wherein $R^{3b}$ is H, wherein $R^{3c}$ is H, wherein $R^{4a}$ is $CF_3$, wherein $R^{4c}$ is H, and wherein $R^{4d}$ is H;

a compound wherein $R^1$ is $CH_3$, wherein $R^2$ is

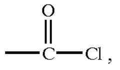

wherein $R^{3b}$ is H, wherein $R^{3c}$ is H, wherein $R^{4a}$ is $CF_3$, wherein $R^{4c}$ is H, and wherein $R^{4d}$ is H;

a compound wherein $R^1$ is

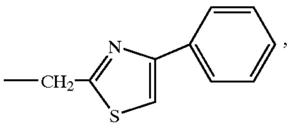

wherein $R^2$ is

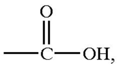

wherein $R^{3b}$ is H, wherein $R^{3c}$ is H, wherein $R^{4a}$ is H, wherein $R^{4c}$ is H, and wherein $R^{4d}$ is H;

a compound wherein $R^1$ is $CH_3$, wherein $R^2$ is CN, wherein $R^{3b}$ is Cl, wherein $R^{3c}$ is H, wherein $R^{4a}$ is $CF_3$, wherein $R^{4c}$ is H, and wherein $R^{4d}$ is H;

a compound wherein $R^1$ is $CH_3$, wherein $R^2$ is CN, wherein $R^{3b}$ is Cl, wherein $R^{3c}$ is H, wherein $R^{4a}$ is $CF_3$ wherein $R^{4c}$ is H and wherein $R^{4d}$ is H;

a compound wherein $R^1$ is $CH_3$, wherein $R^2$ is

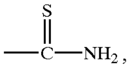

wherein $R^{3b}$ is H, wherein $R^{3c}$ is H, wherein $R^{4a}$ is $CH_3$, wherein $R^{4c}$ is H, and wherein $R^{4d}$ is H;

a compound wherein $R^1$ is H, wherein $R^2$ is

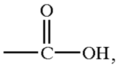

wherein $R^{3b}$ is Cl, wherein $R^{3c}$ is H, wherein $R^{4a}$ is $CF_3$, wherein $R^{4c}$ is H, and wherein $R^{4d}$ is H;

a compound wherein $R^1$ is H, wherein $R^2$ is

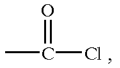

wherein $R^{3b}$ is Cl, wherein $R^{3c}$ is H, wherein $R^{4a}$ is $CF_3$, wherein $R^{4c}$ is H, and wherein $R^{4d}$ is H;

a compound wherein $R^1$ is $(CH_2)_3$—$N(CH_3)_2$, wherein R is CN, wherein $R^{3b}$ is H, wherein $R^{3c}$ is H, wherein $R^{4a}$ is H, wherein $R^{4c}$ is H, and wherein $R^{4d}$ is H;

a compound wherein $R^1$ is H, wherein $R^2$ CN, wherein $R^{3b}$ is Cl wherein $R^{3c}$ is H, wherein $R^{4a}$ is $CH_3$, wherein $R^{4c}$ is H, and wherein $R^{4d}$ is H;

a compound wherein $R^1$ is H, wherein $R^2$ is

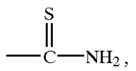

wherein $R^{3b}$ is Cl, wherein $R^{3c}$ is H, wherein $R^{4a}$ $CH_3$, wherein $R^{4c}$ is H, and wherein $R^{4d}$ is H;

a compound wherein $R^1$ is H, wherein $R^2$ is

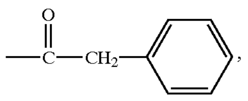

wherein $R^{3b}$ is Cl, wherein $R^{3c}$ is H, wherein $R^{4a}$ is H, wherein $R^{4c}$ is H, and wherein $R^{4d}$ is H;

a compound wherein $R^1$ is H, wherein $R^2$ is

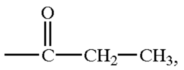

wherein $R^{3b}$ is Cl, wherein $R^{3c}$ is H, wherein $R^{4a}$ is H, wherein $R^{4c}$ is H, and wherein $R^{4d}$ is H;

a compound wherein $R^1$ is $CH_3$, wherein $R^2$ is CN, wherein $R^{3b}$ is Cl, wherein $R^{3c}$ is H, wherein $R^{4a}$ is F, wherein $R^{4c}$ is H, and wherein $R^{4d}$ is H;

a compound wherein $R^1$ is $CH_3$, wherein $R^2$ is

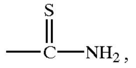

wherein $R^{3b}$ is Cl, wherein $R^{3c}$ is H, wherein $R^{4a}$ is F, wherein $R^{4c}$ is H, and wherein $R^{4d}$ is H;

a compound wherein $R^1$ is H, wherein $R^2$ is CN, wherein $R^{3b}$ is Cl, wherein $R^{3c}$ is H, wherein $R^{4a}$ is $CH_3O$, wherein $R^{4c}$ is H, and wherein $R^{4d}$ is H;

a compound wherein $R^1$ is H, wherein $R^2$ is

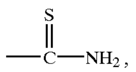

wherein $R^{3b}$ is Cl, wherein $R^{3c}$ is H, wherein $R^{4a}$ is $CH_3O$, wherein $R^{4c}$ is H, and wherein $R^{4d}$ is H;

a compound wherein $R^1$ is H, wherein $R^2$ is

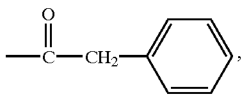

wherein $R^{3b}$ is H, wherein $R^{3c}$ is H, wherein $R^{4a}$ is H, wherein $R^{4c}$ is H, and wherein $R^{4d}$ is H;

a compound wherein $R^1$ is $CH_3$, wherein $R^2$ is

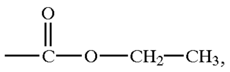

wherein $R^{3b}$ is Cl, wherein $R^{3c}$ is H, wherein $R^{4a}$ is H, wherein $R^{4c}$ is H, and wherein $R^{4d}$ is H;

a compound wherein $R^1$ is $CH_3$, wherein $R^2$ is

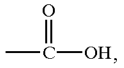

wherein $R^{3b}$ is Cl, wherein $R^{3c}$ is H, wherein $R^{4a}$ is H, wherein $R^{4c}$ is H, and wherein $R^{4d}$ is H;

a compound wherein $R^1$ is $CH_3$, wherein $R^2$ is

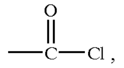

wherein $R^{3b}$ is Cl, wherein $R^{3c}$ is H, wherein $R^{4a}$ is H, wherein $R^{4c}$ is H, and wherein $R^{4d}$ is H; and enantiomers, diastereomers, tautomers, solvates, and pharmaceutically acceptable salts thereof.

15. A method for treating an eosinophil-dependent inflammatory disease in a warm-blooded animal in need thereof comprising administering to the warm-blooded animal an effective amount of a compound of the following Formula:

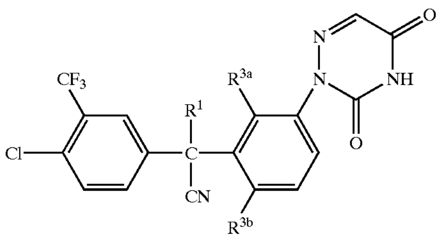

wherein said compound is selected from the group consisting of:

a compound wherein $R^1$ is $CH_3$, wherein $R^{3a}$ is H, and wherein $R^{3b}$ is Cl;

a compound wherein $R^1$ is $CH_3$, wherein $R^{3a}$ is Cl, and wherein $R^{3b}$ is H;

a compound wherein $R^1$ is H, wherein $R^{3a}$ is H, and wherein $R^{3b}$ is Cl;

a compound wherein $R^1$ is H, wherein $R^{3a}$ is Cl, and wherein $R^{3b}$ is H; and enantiomers, diastereomers, tautomers, solvates, and pharmaceutically acceptable salts thereof.

16. A method for treating an cosinophil-dependent inflammatory disease in a warm-blooded animal in need thereof comprising administering to the warm-blooded animal an effective amount of a compound of the following Formula:

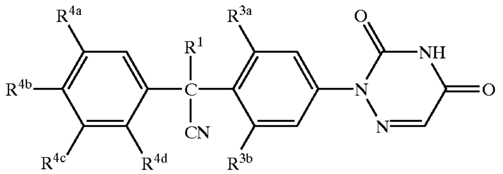

wherein said compound is selected from the group consisting of:

a compound wherein $R^1$ is H, wherein $R^{3a}$ is Cl, wherein $R^{3b}$ is Cl, wherein $R^{4a}$ is H, wherein $R^{4b}$ is H, wherein $R^{4c}$ is H, and wherein $R^{4d}$ is H;

a compound wherein $R^1$ is H, wherein $R^{3a}$ is Cl, wherein $R^{3b}$ is Cl, wherein $R^{4a}$ is H, wherein $R^{4b}$ is $OCH_3$, wherein $R^{4c}$ is H, and wherein $R^{4d}$ is H;

a compound wherein $R^1$ is H, wherein $R^{3a}$ is H, wherein $R^{3b}$ is H, wherein $R^{4a}$ is H, wherein $R^{4b}$ is Cl, wherein $R^{4c}$ is H, and wherein $R^{4d}$ is H;

$CH_3$, wherein $R^{3a}$ is Cl, wherein $R^{3b}$ is H, wherein $R^{4a}$ is $OCH_3$, wherein $R^{4b}$ is $OCH_3$, wherein $R^{4c}$ is H, and wherein $R^{4d}$ is H;

a compound wherein $R^1$ is $CH_3$, wherein $R^{3a}$ is Cl, wherein $R^{3b}$ is H, wherein $R^{4a}$ is H, wherein $R^{4b}$ is $OCH_3$, wherein $R^{4c}$ is H, and wherein $R^{4d}$ is H;

a compound wherein $R^1$ is $CH_3$, wherein $R^{3a}$ is Cl, wherein $R^{3b}$ is H, wherein $R^{4a}$ is Cl, wherein $R^{4b}$ is $OCH_3$, wherein $R^{4c}$ is H, and wherein $R^{4d}$ is H;

a compound wherein $R^1$ is $CH_3$, wherein $R^{3a}$ is $OCH_3$, wherein $R^{3b}$ is H, where in $R^{4a}$ is $CF_3$, wherein $R^{4b}$ is Cl, wherein $R^{4c}$ is H, and wherein $R^{4d}$ is H;

a compound wherein $R^1$ is $CH_3$, wherein $R^{3a}$ is Cl, wherein $R^{3b}$ is H, wherein $R^{4a}$ is $OCH_3$, wherein $R^{4b}$ is $OCH_3$, wherein $R^{4c}$ is $OCH_3$, and wherein $R^{4d}$ is H;

a compound wherein $R^1$ is $CH_3$, wherein $R^{3a}$ is Cl, wherein $R^{3b}$ is H, wherein $R^{4a}$ is $CH_3$, wherein $R^{4b}$ is $OCH_3$, wherein $R^{4c}$ is H, and wherein $R^{4d}$ is H;

a compound wherein $R^1$ is $CH_3$, wherein $R^{3a}$ is H, wherein $R^{3b}$ is H, wherein $R^{4a}$ is H, wherein $R^{4b}$ is Cl, wherein $R^{4c}$ is H, and wherein $R^{4d}$ is Cl;

a compound wherein $R^1$ is $CH_3$, wherein $R^{3a}$ is $CH_3$ wherein $R^{3b}$ is H, wherein $R^{4a}$ is $CF_3$, wherein $R^{4b}$ is Cl, wherein $R^{4c}$ is H, and wherein $R^{4d}$ is H;

a compound wherein $R^1$ is $CH_3$, wherein $R^{3a}$ is Cl, wherein $R^{3b}$ is H, wherein $R^{4a}$ is H, wherein $R^{4b}$ is phenyl, wherein $R^{4c}$ is H, and wherein $R^{4d}$ is H;

a compound wherein $R^1$ is H, wherein $R^{3a}$ is Cl, wherein $R^{3b}$ is Cl, wherein $R^{4a}$ is $CF_3$, wherein $R^{4b}$ is Cl wherein $R^{4c}$ is H, and wherein $R^{4d}$ is H;

a compound wherein $R^1$ is

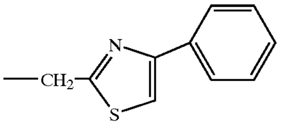, wherein $R^{3a}$ is Cl, wherein $R^{3b}$ is H, wherein $R^{4a}$ is H, wherein $R^{4b}$ is Cl, wherein $R^{4c}$ is H, and wherein $R^{4d}$ is H;

H, wherein $R^{3a}$ is $CH_3$, wherein $R^{3b}$ is $CH_3$, wherein $R^{4a}$ is Cl, wherein $R^{4b}$ is Cl, wherein $R^{4c}$ is H, and wherein $R^{4d}$ is H;

a compound wherein $R^1$ is H, wherein $R^{3a}$ is Br, wherein $R^{3b}$ is Br, wherein $R^{4a}$ is H, wherein $R^{4b}$ is Cl, wherein $R^{4c}$ is H, and wherein $R^{4d}$ is H; and enantiomers, diastereomers, tautomers, solvates, and pharmaceutically acceptable salts thereof.

17. A method for treating an eosinophil-dependent inflammatory disease in a warm-blooded animal in need thereof comprising administering to the warm-blooded animal an effective amount of a compound of the following Formula:

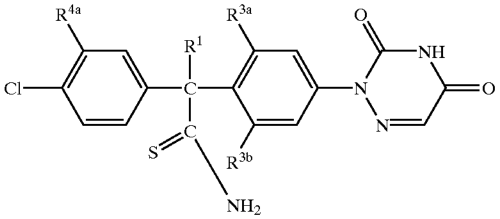

wherein said compound is selected from the group consisting of:

a compound wherein $R^1$ is $CH_3$, wherein $R^{3a}$ is $CH_3O$, wherein $R^{3b}$ is H, and wherein $R^{4a}$ is $CF_3$;

a compound wherein $R^1$ is H, wherein $R^{3a}$ is $CH_3$, wherein $R^{3b}$ is $CH_3$, and wherein $R^{4a}$ is Cl;

a compound wherein $R^1$ is H, wherein $R^{3a}$ is Br, wherein $R^{3b}$ is Br, and wherein $R^{4a}$ is H; and enantiomers, diastereomers, tautomers, solvates, and pharmaceutically acceptable salts thereof.

18. A method for treating an eosinophil-dependent inflammatory disease in a warm-blooded animal in need thereof comprising administering to the warm-blooded animal an effective amount of a compound of the following Formula:

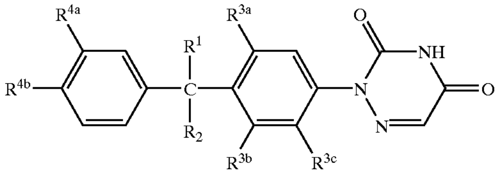

wherein said compound is selected from the group consisting of:

a compound wherein $R^1$ is $CH_3$, wherein $R^2$ is CN, wherein $R^{3a}$ is H, wherein $R^{3b}$ is H, wherein $R^{3c}$ is H, wherein $R^{4a}$ is H and wherein $R^{4b}$ is H;

a compound wherein $R^1$ is $CH_3$, wherein $R^2$ is CN, wherein $R^{3a}$ is Cl, wherein $R^{3b}$ is H, wherein $R^{3c}$ is H, wherein $R^{4a}$ is H, and wherein $R^{4b}$ is F;

a compound wherein $R^1$ is $CH_3$, wherein $R^2$ is CN, wherein $R^{3a}$ is $CF_3$, wherein $R^{3b}$ is H, wherein $R^{3c}$ is H, wherein $R^{4a}$ is H, herein $R^{4b}$ is Cl;

a compound wherein $R^1$ is 4-chlorophenyl, wherein $R^2$ is CN, wherein $R^{3a}$ is Cl, wherein $R^{3b}$ is H, wherein $R^{3c}$ is H, wherein $R^{4a}$ is H, and wherein $R^{4b}$ is Cl;

a compound wherein $R^1$ is $(CH_2)_2$-$CH_3$, wherein $R^2$ is CN, wherein $R^{3a}$ is Cl, wherein $R^{3b}$ is H, wherein $R^{3c}$ is H, wherein $R^{4a}$ is H, and wherein $R^{4b}$ is Cl;

a compound wherein $R^1$ is $(CH_2)_3$-$CH_3$, wherein $R^2$ is CN, wherein $R^{3a}$ is Cl, wherein $R^{3b}$ is H, wherein $R^{3c}$ is H, wherein $R^{4a}$ is H, and wherein $R^{4b}$ is Cl;

a compound wherein $R^1$ is $CH_3$, wherein $R^2$ is CN, wherein $R^{3a}$ is Cl, wherein $R^{3b}$ is H, wherein $R^{3c}$ is H, wherein $R^{4a}$ is $CF_3$ and wherein $R^{4b}$ is Cl;

a compound wherein $R^1$ is $CH_3$, wherein $R^2$ is CN, wherein $R^{3a}$ is Cl, wherein $R^{3b}$ is Cl, wherein $R^{3c}$ is H, wherein $R^{4a}$ is H, and wherein $R^{4b}$ is Cl;

a compound wherein $R^1$ is H, wherein $R^2$ is CN, wherein $R^{3a}$ is Cl, wherein $R^{3b}$ is H, wherein $R^{3c}$ is H, wherein $R^{4a}$ is H, and wherein $R^{4b}$ is Cl;

a compound wherein $R^1$ is $CH_3$, wherein $R^2$ is CN, wherein $R^{3a}$ is Cl, wherein $R^{3b}$ is $CH_3$, wherein $R^{3c}$ is H, wherein $R^{4a}$ is H, wherein $R^{4b}$ is Cl;

a compound wherein $R^1$ is $CH_3$, wherein $R^2$ is CN, wherein $R^{3a}$ is Cl, wherein $R^{3b}$ is H, wherein $R^{3c}$ is $CH_3$, wherein $R^{4a}$ is H, and wherein $R^{4b}$ is Cl;

a compound wherein $R^1$ is H, wherein $R^2$ is CN, wherein $R^{3a}$ is Cl, wherein $R^{3b}$ is Cl, wherein $R^{3c}$ is H, wherein $R^{4a}$ is H, and wherein $R^{4b}$ is Cl;

a compound wherein $R^1$ is H, wherein $R^2$ is CN, wherein $R^{3a}$ is Cl, wherein $R^{3b}$ is H, wherein $R^{3c}$ is H, wherein $R^{4a}$ is H, and wherein $R^{4b}$ is F;

a compound wherein $R^1$ is H, wherein $R^2$ is CN, wherein $R^{3a}$ is Cl, wherein $R^{3b}$ is H, wherein $R^{3c}$ is H, wherein $R^{4a}$ is H, and wherein $R^{4b}$ is $CH_3$;

a compound wherein $R^1$ is $CH_3$, wherein $R^2$ is CN, wherein $R^{3a}$ is F, wherein $R^{3b}$ is H, wherein $R^{3c}$ is H, wherein $R^{4a}$ is H, and wherein $R^{4b}$ is F;

a compound wherein $R^1$ is H, wherein $R^2$ is CN, wherein $R^{3a}$ is Cl, wherein $R^{3b}$ is Cl, wherein $R^{3c}$ is H, wherein $R^{4a}$ is H, and wherein $R^{4b}$ is F;

a compound wherein $R^1$ is H, wherein $R^2$ is CN, wherein $R^{3a}$ is Cl, wherein $R^{3b}$ is $CH_3$, wherein $R^{3c}$ is H, wherein $R^{4a}$ is H, and wherein $R^{4b}$ is F;

a compound wherein $R^1$ is H, wherein $R^2$ is CN, wherein $R^{3a}$ is $CH_3$, wherein $R^{3b}$ is $CH_3$, wherein $R^{3c}$ is H, wherein $R^{4a}$ is H, wherein $R^{4b}$ is F;

a compound wherein $R^1$ is H, wherein $R^2$ is CN, wherein $R^{3a}$ is $CH_3$, wherein $R^{3b}$ is $CH_3$, wherein $R^{3c}$ is H, wherein $R^{4a}$ is H, and wherein $R^{4b}$ is Cl;

a compound wherein $R^1$ is H, wherein $R^2$ is C(=O)NHCH$_3$, wherein $R^{3a}$ is Cl, wherein $R^{3b}$ is Cl, wherein $R^{3c}$ is H, wherein $R^{4a}$ is H, and wherein $R^{4b}$ is Cl;

a compound wherein $R^1$ is H, wherein $R^2$ is

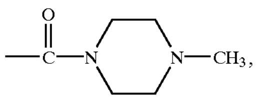

wherein $R^{3a}$ is Cl, wherein $R^{3b}$ is Cl, wherein $R^{3c}$ is H, wherein $R^{4a}$ is H, and wherein $R^{4b}$ is Cl;

a compound wherein $R^1$ is H, wherein $R^2$ is C(=O)CH$_3$, wherein $R^{3a}$ is Cl, wherein $R^{3b}$ is Cl, wherein $R^{3c}$ is H, wherein $R^{4a}$ is H, and wherein $R^{4b}$ is Cl;

a compound wherein $R^1$ is H, wherein $R^2$ is C(=S)NH$_2$, wherein $R^{3a}$ is Cl, wherein $R^{3b}$ is Cl, wherein $R^{3c}$ is H, wherein $R^{4a}$ is H, and wherein $R^{4b}$ is Cl; and enantiomers, diastereomers, tautomers, solvates, and pharmaceutically acceptable salts thereof.

* * * * *